United States Patent [19]
Rice et al.

[11] Patent Number: 5,874,565
[45] Date of Patent: Feb. 23, 1999

[54] NUCLEIC ACIDS COMPRISING A HIGHLY CONSERVED NOVEL 3 TERMINAL SEQUENCE ELEMENT OF THE HEPATITIS C VIRUS

[75] Inventors: Charles M. Rice, University City; Alexander A. Kolykhalov, St. Louis, both of Mo.

[73] Assignee: Washington University, St. Louis, Mo.

[21] Appl. No.: 520,678

[22] Filed: Aug. 29, 1995

[51] Int. Cl.[6] .......................... C07H 21/02; C07H 21/04; C12Q 1/68; C12N 15/00
[52] U.S. Cl. ...................... 536/24.1; 536/23.1; 536/24.3; 536/24.33; 435/6; 435/172.3
[58] Field of Search .............................. 435/91.32, 91.33, 435/252.3; 536/23.1, 24.1, 24.3

[56] References Cited

FOREIGN PATENT DOCUMENTS

| | | |
|---|---|---|
| 510952 | 10/1992 | European Pat. Off. . |
| 521318 | 1/1993 | European Pat. Off. . |
| 645451 | 3/1995 | European Pat. Off. . |
| WO 93/03186 | 2/1993 | WIPO . |

OTHER PUBLICATIONS

Bukh et al (1995) Sem. Liver Dis. 15:41–63.
Boyer and Haenni (1994) J. Gen. Virol. 198: 415–426.
Bresters et al (1994) J. Med. Virol. 43:262–8.
Chazouilleres et al (1994) Gastroenterology 106:994–9.
Davis et al (1994) Hepatology 19:1337–41.
Feray et al (1994) Hepatology 20:1137–43.
Gordon et al (1994) Am. J. Gastroenterol. 89:1458–61.
Lin et al (1994) J. Virol. 68:5063–5073.
Okamoto et al (1994) J. Gen. Virol. 75:629–635.
Sakamoto et al (1994) J. Gen. Virol. 75:1761–1768.
Simmonds et al (1994) J. Gen. Virol. 75:1053–1061.
Tokita et al (1994) J. Gen. Virol. 75:931–936.
Wright et al (1994) Hepatology 20:773–9.
Chen et al (1992) Virology 188:102–113.
Cha et al (1991) J. Clin. Microbiol. 29:2528–34.
Inchauspe et al (1991) Proc. Natl. Acad. Sci. USA 88:10292–10296.
Mandl et al (1991) Biotechniques 10:486.
Okamoto et al (1991) J. Gen. Virol. 72:2697–2704.
Chambers et al (1990) Virology 177:159–174.
Sullenger et al (1990) Cell 63:601–608.
Umlauft et al., Hepatitis C Virus Detection by Single–Round PCR Specific for the Terminal 3' Noncoding Region, *J. Clin. Micro.*, 34:2552–2558 (1996).
Choo et al. (1995) Proc. Natl. Acad. Sci. USA 88:2451–5.
Han et al. (1991) Proc. Natl. Acad. Sci. USA 88:1711–5.
Yoo et al. (1995) J. Virology 69:32–8.
Hahn et al. (1987) J. Mol. Biol. 198:33–41.
Kolykhalov et al. (1996) J. Virology 70:3363–71.
Tanaka et al. (1995) Biochem. Biophys. Res. Commun. 215:744–9.
Tanaka et al. (1996) J. virology 70:3307–12.
Reeck et al., 1987, Cell 50:667.
Lewin, 1987, Science 237:1570.
Strongin, W., 1993, "Sensitivity, Specificity, and Predictive Value of Diagnostic Tests: Definitions and Clinical Applications", in *Laboratory Diagnosis of Viral Infections*, Lennette, E., ed., Marcel Dekker, Inc., New York, pp. 211–219.

*Primary Examiner*—Laurie Scheiner
*Assistant Examiner*—Jeffrey S. Parkin
*Attorney, Agent, or Firm*—Howell & Haferkamp, L.C.

[57] ABSTRACT

The invention relates to the discovery of a novel RNA sequence at the 3' terminal sequence of hepatitis C virus (HCV) genome RNA. Included in the invention are the 3' sequence, its complement, and their use for nucleic-acid based diagnostics and for developing and evaluating novel anti-HCV therapies. This sequence element, which is conserved among HCV genotypes, is likely to be essential for viral replication, and required for construction of full-length HCV cDNA clones capable of yielding infections RNA, progeny virus or replication-competent HCV replicons. Such functional clones are useful tools for evaluation of therapeutic approaches and as substrates for developing candidate attenuated or inactivated HCV derivatives for vaccination against HCV.

17 Claims, 10 Drawing Sheets

```
HCV-H(1a)      TGAagattgggctaaccactcc
               ::::: ::::::  :::  :::::::
HCV-1(1a)      TGAaggttggggtaaacactcc-ggcct(an)
               ::::::::::::::::::::::::::::
HCV-H-AAK      TGAaggttggggtaaacactcc-ggcctctcttaggccattcctgt(tn)
               ::  :::::::::::::::::::::::::::::  ::::
HCV-J1(1a)     TAAaggttggggtaaacactcc-ggcctcttaggccatttctgtg(tn)
HCV-BK(1b)     TGAacggggagataaacactccaggccaa-taggccatcccc(tn)
HCV-TW(1b)     TGAacggggagctaaacactccaggccaa-taggccatcctg(tn)
HCV-N(1b)      TGAacggggagctaaacactccag-ccaa-taggccatttcctttg(tn)
HCV-J6(2a)     TAGagcggcacac-ttagctacactcca--tagctaactgtccc(tn)
HCV-J8(2b)     TAGagcggcaaaccctagctacactcca--tagctagtttccg(tn)
HCV-NZL1(3a)   TGAgctggtaagataacactcca-------tttcttttttg(tn)
HCV-Tr(3b)     TGAgctggtaggttaacacaccccca---------acccgtg(tn)
```

Figure 2

```
H77-#1.2   GTGTCTCATGCCCGGCCCCGCTGGTTCTGGTTTTGCCTACTCCTGCTCAC
  H77-#8   GTGTCTCATGCCCGGCCCCGCTGGTTCTGGTTTTGCCTACTCCTGCTCGC
 H77-#10   GTGTCTCATGCCCGGCCCCGCTGGTTCTGGTTTTGCCTACTCCTGCTCGC
 H77-#74   GTGTCTCATGCCCGGCCCCGCTGGTTCTGGTTTTGCCTACTCCTGCTCGC
  H77-#5   GTGTCTCATGCCCGGCCCCGCTGGTTCTGGTTTTGCCTACTCCTGCTTGC

H77-#1.2   TGCAGGGGTAGGTATCTACCTCCTCCCCAACCGATGAAGGTTGGGGTAAA
  H77-#8   TGCAGGGGTAGGCATCTACCTCCTCCCCAACCGATGAAGGTTGGGGTAAA
 H77-#10   TGCAGGGGTAGGCATCTACCTCCTCCCCAACCGATGAAGGTTGGGGTAAA
 H77-#74   TGCAGGGGTAGGCATCTACCTCCTCCCCAACCGATGAAGGTTGGGGTAAA
  H77-#5   TGCAGGGGTAGGCATCTACCTCCTCCCCAACCGATGAAGGTTGGGGTAAA

H77-#1.2   CACTCCGGCCTCTTAGGCCATTTCCTGTTTTTTTTTTTTTTTTTT...
  H77-#8   CACTCCGGCCTCTTAGGCCATTTCCTGTTTTTTTTTTTTTTTTTTTTTT
 H77-#10   CACTCCGGCCTCTTAGGCCATTTCCTGTTTTTTTTTTTTTTTTTTTTTT
 H77-#74   CACTCCGGCCTCTTAGGCCATTTCCTGTTTTTTTTTTTTTCCCTTTTTT
  H77-#5   CACTCCGGCCTCTTAGGCCATTTCCTGTTTTTTTTTTTTTTTTTTTTTT

H77-#1.2   ..................................................
  H77-#8   TTTTTTTTTTT.......................................
 H77-#10   TTTTTTTTTTTTTTTTTTTTTTTTTTCTTTTTTTTTTTTTTTTTCCTT
 H77-#74   TTTTTTTTTTTTTTTTTTTTTTTTTTTT......................
  H77-#5   TTTTTTTTTTTTTTTTTTTTTTTTTTT.......................

H77-#1.2   ..................CTTTCCTTCTTTTT..CCTTTCTTTTCCTTC
  H77-#8   ...................CTTTTCCTTCTTTTTC..CCTTTTTCTTTCTTC
 H77-#10   TTTTTTTTTTTTTTTTCTTTCCTTCTTTTTT..CCTTTCTTTTCCTTC
 H77-#74   ..................CTTTCCTTCTTTTTTTTCCTTTCTTTTCCTTC
  H77-#5   ..................CTTTCCTTCCTTTTCC.CTTTTCTTTTC.TTC

H77-#1.2   CTTCTTTAATGGTGGCTCCATCTTAGCCCTAGTCACGGCTAGCTGTGAAA
  H77-#8   CTTCTTTAATGGTGGCTCCATCTTAGCCCTAGTCACGGCTAGCTGTGAAA
 H77-#10   CTTCTTTAATGGTGGCTCCATCTTAGCCCTAGTCACGGCTAGCTGTGAAA
 H77-#74   CTTCTTTAATGGTGGCTCCATCTTAGCCCTAGTCACGGCTAGCTGTGAAA
  H77-#5   CTTCTTTAATGGTGGCTCCATCTTAGCCCTAGTCACGGCTAGCTGT

H77-#1.2   GGTCCGTGAGCCGCATGACTGCAGAGAGTGCTGATACTGGCCTCTCTGCA
  H77-#8   GGTCCGTGAGCCGCATGACTGCAGAGAGTGCTGATACTGGCCTCTCTGCA
 H77-#10   GGTCCGTGAGCGGCATGACTGCAGAGAGTGCTGATACTGGCCTCTCCGCA
 H77-#74   GGTCCGTGAGCGGCATGACTGCAGAGAGTGCTGATACTGGCCTCTCTGCT
  H77-#5

H77-#1.2   GATCATGT
  H77-#8   GATCATGT
 H77-#10   GATCATGT
 H77-#74   GATCATGT
  H77-#5
```

Figure 3

```
        1                                                                    50
1b      CTGTCTCGTG  CCCGACCCCG  CTGGTTCATG  TTGTGCCTAC  TCCTACTTTC
3       GTGTCACGTG  CCCGAACCCG  CTATTTGCTG  CTTTGCCTAC  TCCTACTAAC
4?      GTGTCCCATG  CCCGACCCCG  CTATCTACTC  CTGTGCCTAC  TCCTACTTTC
4a      ATGTCTCATG  CCCGACCCCG  CTATTTACTC  CTGTGCCTAC  TCCTACTTAC 51                                                                   100
1b      CGTAGGGGTA  GGCATCTACC  TGCTCCCCAA  CCGATGAA..  CGGGGAGCTA
3       GGTAGGGGTA  GGCATCTTTC  TCCTGCCAGC  GCGATGAGCT  GGTAGG.ATA
4?      CGTAGGGGTA  GGCATCTTCC  TGCTGCCTGC  TCGATAGGCA  GCT.....TA
4a      AGTAGGGGTA  GGCATCTTCC  TGCTGCCTGC  TCGGTAGGCA  GCT.....TA 101                                                                  150
1b      ACACTCCAGG  CCAATAGG.C  AT..CCTGTT  TTTTTTTTTT  TTTTTTTTTT
3       ACACT.....  ........CC  ATTTCTTTT   TTGTTTTTTT  TTTTTTTTTT
4?      ACACTCCGAC  CT..TAGGGT  CCTTC.TGTT  TTTTTTTTTT  TTTTTTTTTT
4a      ACACTCCGAC  CT..TAGGGT  CCCCT.TGTT  TTTTTTTTTT  ..........

151                                                                  200
1b      TTTTTTTTTT  TTTTTTTTTT  TTTTTTTTTT  TTTTTTTTTT  TT........
3       TTTTTTTTTT  TTTTTTTTTT  TTTTTTTTTT  TTTTTTTTTT  TTTTTTTTTT
4?      TTTTTTTTTT  TTTTTTTTTT  TTTTTTTTTT  TTTTTTTTTT  TTTTTTTTTT
4a      ..........  ..........  ..........  ..........  ..........

201                                                                  250
1b      ..........  ..........  ..........  ..........  .CTTTTCTTT
3       ...CTTTTTC  TTTCCTTTCT  TTTCTGACTT  CTAATT..TT  CCTTCTT..A
4?      TTTTTTCCTT  ACCCTTTCCT  TCTTTTCTTC  CTTTTTTTTC  CTTACTTT..
4a      .........C  TTTCCTTCTT  T...CCTTTC  CTAAT.CTTT  CTTTCTT...

251
1b      GGTGGCTCCA  TCTTAGCCCT  AGTCACGGCT  A
3       GGTGGCTCCA  TCTTAGCCCT  AGTCACGGCT  A
4?      GGTGGCTCCA  TCTTAGCCCT  AGTCACGGCT  A
4a      GGTGGCTCCA  TCTTAGCCCT  AGTCACGGCT  A
```

Figure 6

| | | | | | |
|---|---|---|---|---|---|
| 1b | GCTGTGAAAG | GTCCGTGAGC | CGCATGACTG | CAGAGAGTGC | TGAAACTGGC CTCTCT |
| 3  | GCTGTGAAAG | GTCCGTGAGC | CGCTTGACTG | CAGAGAGTGC | TGATACTGGC CTCTCT |
| 4? | GCTGTGAAAG | GTCCGTGAGC | CGCATGACTG | CAGAGAGTGC | TGATACTGGC CTCTCT |
| 4a | GCTGTGAAAG | GTCCGTGAGC | CGCATGACTG | CAGAGAGTGC | TGAAACTGGC CTCTCT |

| | | |
|---|---|---|
| 1b | CTCTCTGCA | GATCATGT |
| 3  | CTCTCTGCA | GATCAAGT |
| 4? | CTCTCTGCA | GATCATGT |
| 4a | CTCTCTGCA | GATCATGT |

Figure 8

NUCLEIC ACIDS COMPRISING A HIGHLY CONSERVED NOVEL 3 TERMINAL SEQUENCE ELEMENT OF THE HEPATITIS C VIRUS

GOVERNMENTAL SUPPORT

This work was supported by National Cancer Institute/National Institutes of Health grant number CA57973. The government may have certain rights in this invention.

TECHNICAL FIELD OF THE INVENTION

The present invention relates generally to a novel nucleotide sequence element identified at or near the 3' terminus of the hepatitis C virus (HCV) viral genome RNA. This element is highly conserved among HCV genotypes and may be essential for HCV replication.

BACKGROUND OF THE INVENTION

After the development of diagnostic tests for hepatitis A virus and hepatitis B virus, an additional agent, which could be experimentally transmitted to chimpanzees (Alter et al, 1978; Hollinger et al, 1978; Tabor et al, 1978), became recognized as the major cause of transfusion-acquired hepatitis. cDNA clones corresponding to the causative non-A non-B (NANB) hepatitis agent, called hepatitis C virus (HCV), were reported in 1989 (Choo et al, 1989). This breakthrough has led to rapid advances in diagnostics, and in our understanding of the epidemiology, pathogenesis and molecular virology of HCV (see Houghton et al, 1994 for review). Evidence of HCV infection is found throughout the world and the prevalence of anti-HCV antibodies ranges from 0.4–2% in most developed countries to more than 14% in Egypt (Hibbs et al, 1993). Besides transmission via blood or blood products, or less frequently by sexual and congenital routes, sporadic cases, not associated with known risk factors, occur and account for more than 40% of HCV cases (Alter et al, 1990; Mast and Alter, 1993). Infections are usually chronic (Alter et al, 1992) and clinical outcomes range from an inapparent carrier state to acute hepatitis, chronic active hepatitis, and cirrhosis which is strongly associated with the development of hepatocellular carcinoma. Although alpha IFN has been shown to be useful for the treatment of some patients with chronic HCV infections (Davis et al, 1989; DiBisceglie et al, 1989) and subunit vaccines show some promise in the chimpanzee model (Choo et al, 1994), future efforts are needed to develop more effective therapies and vaccines. The considerable diversity observed among different HCV isolates (for review, see Bukh et al, 1995), the emergence of genetic variants in chronically infected individuals (Enomoto et al, 1993; Hijikata et al, 1991; Kato et al, 1992; Kato et al, 1993; Kurosaki et al, 1993; Lesniewski et al, 1993; Ogata et al, 1991; Weiner et al, 1991; Weiner et al, 1992), and the lack of protective immunity elicited after HCV infection (Farci et al, 1992; Prince et al, 1992) present major challenges towards these goals.

Molecular biology of HCV

Classification. Based on its genome structure and virion properties, HCV has been classified as a separate genus in the flavivirus family, which includes two other genera: the flaviviruses [such as yellow fever virus (YF)] and the animal pestiviruses [bovine viral diarrhea virus (BVDV) and classical swine fever virus (CSFV)] (Francki et al, 1991). All members of this family have enveloped virions that contain a positive-strand RNA genome encoding all known virus-specific proteins via translation of a single long open reading frame (ORF; see below).

Structure and physical properties of the virion. Little information is available on the structure and replication of HCV. Studies have been hampered by the lack of a cell culture system able to support efficient virus replication and the typically low titers of infectious virus present in serum. The size of infectious virus, based on filtration experiments, is between 30–80 nm (Bradley et al, 1985; He et al, 1987; Yuasa et al, 1991). HCV particles isolated from pooled human plasma (Takahashi et al, 1992), present in hepatocytes from infected chimpanzees, and produced in cell culture (Shimizu et al, 1994a) have been visualized (tentatively) by electron microscopy. Initial measurements of the buoyant density of infectious material in sucrose yielded a range of values, with the majority present in a low density pool of <1.1 g/ml (Bradley et al, 1991). Subsequent studies have used RT/PCR to detect HCV-specific RNA as an indirect measure of potentially infectious virus present in sera from chronically infected humans or experimentally infected chimpanzees. From these studies, it has become increasingly clear that considerable heterogeneity exists between different clinical samples, and that many factors can affect the behavior of particles containing HCV RNA (Hijikata et al, 1993; Thomssen et al, 1992). Such factors include association with immunoglobulins (Hijikata et al, 1993) or low density lipoprotein (Thomssen et al, 1992; Thornssen et al, 1993). In highly infectious acute phase chimpanzee serum, HCV-specific RNA is usually detected in fractions of low buoyant density (1.03–1.1 g/ml) (Carrick et al, 1992; Hijikata et al, 1993). In other samples, the presence of HCV antibodies and formation of immune complexes correlate with particles of higher density and lower infectivity (Hijikata et al, 1993). Treatment of particles with chloroform, which inactivates infectivity (Bradley et al, 1983; Feinstone et al, 1983), or with nonionic detergents, produces RNA containing particles of higher density (1.17–1.25 g/ml) believed to represent HCV nucleocapsids (Hijikata et al, 1993; Kanto et al, 1994; Miyamoto et al, 1992).

There have been many reports of varying levels of negative-sense HCV-specific RNAs in sera and plasma (see Fong et al, 1991). However, it seems unlikely that such RNAs are essential components of infectious particles since some sera with high infectivity can have low or undetectable levels of negative-strand RNA (Shimizu et al, 1993). The virion protein composition has not been rigorously determined, but putative HCV structural proteins include a basic C protein and two membrane glycoproteins, E1 and E2.

HCV replication. Early events in HCV replication are poorly understood. Cellular receptors for the HCV glycoproteins have not been identified. The association of some HCV particles with beta-lipoprotein and immunoglobulins raises the possibility that these host molecules may modulate virus uptake and tissue tropism. Studies examining HCV replication have been largely restricted to human patients or experimentally inoculated chimpanzees. In the chimpanzee model, HCV RNA is detected in the serum as early as 3 days post-inoculation and persists through the peak of serum alanine aminotransferase (ALT) levels (an indicator of liver damage) (Shimizu et al, 1990). The onset of viremia is followed by the appearance of indirect hallmarks of HCV infection of the liver. These include the appearance of a cytoplasmic antigen (Shimizu et al, 1990) and ultrastructural changes in hepatocytes such as the formation of microtubular aggregates for which HCV previously was referred to as the chloroform-sensitive "tubule forming agent" or "TFA" (reviewed by Bradley, 1990). As shown by the appearance of viral antigens (Blight et al, 1993; Hiramatsu et al, 1992; Krawczynski et al, 1992; Yamada et al, 1993) and the detection of positive and negative sense RNAs (Fong et al, 1991; Gunji et al, 1994; Haruna et al, 1993; Lamas et al, 1992; Nouri Aria et al, 1993; Sherker et al, 1993; Takehara et al, 1992; Tanaka et al, 1993), hepatocytes appear to be a major site of HCV replication, particularly during acute infection (Negro et al, 1992). In later stages of HCV infection the appearance of HCV-specific antibodies, the persistence or resolution of viremia, and the severity of liver disease, vary greatly both in the chimpanzee model and in human patients. Although some liver damage may occur as a direct consequence of HCV infection and cytopathogenicity, the emerging consensus is that host immune responses, in particular virus-specific cytotoxic T lymphocytes, may play a more dominant role in mediating cellular damage (see Rice and Walker, 1995 for review).

It has been speculated that HCV may also replicate in extra hepatic reservoir(s), particularly in chronically infected individuals. In some cases, RT/PCR or in situ hybridization has shown an association of HCV RNA with peripheral blood mononuclear cells including T-cells, B-cells, and monocytes (Blight et al, 1992; Bouffard et al, 1992; Gil et al, 1993; Gunji et al, 1994; Moldvay et al, 1994; Nuovo et al, 1993; Wang et al, 1992; Young et al, 1993; Yun et al, 1993; Zignego et al, 1992). Such tissue tropism could be relevant to the establishment of chronic infections and might also play a role in the association between HCV infection and certain immunological abnormalities such as mixed cryoglobulinemia (reviewed by Ferri et al, 1993), glomerulonephritis, and rare non-Hodgkin's B-lymplhomas (Ferri et al, 1993; Kagawa et al, 1993). However, the detection of circulating negative strand RNA in serum, the difficulty in obtaining truly strand-specific RT/PCR (Gunji et al, 1994), and the low numbers of apparently infected cells have made it difficult to obtain unambiguous evidence for replication in these tissues in vivo.

Although a cell culture system capable of efficient HCV replication has not been developed, some progress has been made. Consistent with the in vivo observations mentioned above, in vitro HCV infection and short term replication have been reported for chimpanzee and human hepatocytes (Carloni et al, 1993; Iacovacci et al, 1993; Lanford et al, 1994), a human hepatoma line (Huh7; Yoo et al, 1995, see below), peripheral blood leukocytes (Muller et al, 1993), a human B-cell line expressing EBV antigens (Bertolini et al, 1993), a mouse retrovirus-infected human T-cell line (Molt4-Ma; Shimizu et al, 1992), an HTLV-1 transformed human T-cell line (MT-2; Kato et al, 1995), and fibroblasts derived from human foreskin (Zibert et al, 1995). Thus far, only a small fraction of these cells appear infected. In vitro infectivity of different HCV inocula using a permissive subclone of the Molt4-Ma T-cell line correlates well with their in vivo infectivity in the chimpanzee model (Shimizu et al, 1993). This cell line has also been used to begin examining HCV binding and the possible emergence of neutralization escape mutants during chronic infection (Shimizu et al, 1994b).

Genome structure. Full-length or nearly full-length genome sequences of numerous HCV isolates have been reported (see Lin et al, 1994; Okainoto et al, 1994; Sakamoto et al, 1994 and citations therein). Given the considerable genetic divergence among isolates, it is clear that several major HCV genotypes are distributed throughout the world (see below). Those of greatest importance in the U.S. are genotype 1, subtypes 1a and 1b. HCV genome RNAs are about 9.4 kilobases in length. The 5' NTR is 341–344 bases and is the most conserved RNA sequence element in the HCV genorne. The length of the long ORF varies slightly among isolates, encoding polyproteins of 3010, 3011 or 3033 amino acids. The reported 3' NTR structures show considerable diversity both in composition and length (28–42 bases), and appear to terminate with poly (U) (for examples, see Chen et al, 1992; Okamoto et al, 1991; Tokita et al, 1994) except in one case (HCV-1, type 1a) which appears contain a 3' terminal poly (A) tract (Han et al, 1991).

Translation and proteolytic processing. Several studies have used cell-free translation and transient expression in cell culture to examine the role of the 5' NTR in translation initiation (Fukushi et al, 1994; Tsukiyaina-Kohara et al, 1992; Wang et al, 1993; Yoo et al, 1992). This highly conserved sequence contains multiple short AUG-initiated ORFs and shows significant homology with the 5' NTR region of pestiviruses (Bukh et al, 1992; Han et al, 1991). A series of stem-loop structures have been proposed on the basis of computer modeling and sensitivity to digestion by different ribonucleases (Brown et al, 1992; Tsukiyama-Kohara et al, 1992). Although still controversial (see Wang et al, 1993; Yoo et al, 1992), the results from several groups indicate that this element functions as an internal ribosome entry site (IRES) allowing efficient translation initiation at the first AUG of the long ORF (Fukushi et al, 1994; Tsukiyama-Kohara et al, 1992; Wang et al, 1993). Some of the predicted features of the HCV and pestivirus IRES elements are similar to one another (Brown et al, 1992). It has been proposed that the 5' terminal hairpin structure and the short ORFs may function to downregulate translation (Yoo et al, 1992). The ability of this element to function as an IRES suggests that HCV genorne RNAs may lack a 5' cap structure.

The organization and processing of the HCV polyprotein appears to be most similar to that of the pestiviruses. At least 10 polypeptides have been identified and the order of these cleavage products in the polyprotein is $NH_2$-C-E1-E2-p7-NS2-NS3-NS4A-NS4B-NS5A-NS5B-COOH. Proteolytic processing is mediated by host signal peptidase and two HCV-encoded proteinases, the NS2-3 autoproteinase and the NS3-4A serine proteinase. C is a basic protein believed to be the viral core or capsid protein; E1 and E2 are putative virion envelope glycoproteins; p7 is a hydrophobic protein of unknown function that is inefficiently cleaved from the E2 glycoprotein (Lin et al, 1994; Mizushima et al, 1994; Selby et al, 1994), and NS2-NS5B are likely nonstructural (NS) proteins which function in viral RNA replication complexes. In particular, besides its N-terminal serine proteinase domain, NS3 contains motifs characteristic of RNA helicases and has been shown to possess an RNA-stimulated NTPase activity (Suzich et al, 1993); NS5B contains the GDD motif characteristic of the RNA-dependent RNA polymerases of positive-strand RNA viruses.

Virion assembly and release. This process has not been examined directly, but the lack of complex glycans, the ER localization of expressed HCV glycoproteins (Dubuisson et al, 1994; Ralston et al, 1993) and the absence of these proteins on the cell surface (Dubuisson et al, 1994; Spaete et al, 1992) suggest that initial virion morphogenesis may occur by budding into intracellular vesicles. Thus far, efficient particle formation and release has not been observed in transient expression assays, suggesting that essential viral or host factors are missing or blocked. HCV virion formation and release may be inefficient, with a substantial fraction of the virus remaining cell-associated, as found for the pestiviruses. A recent study indicates that extracellular HCV particles partially purified from human plasma do contain complex N-linked glycans, although these carbohydrate moieties were not shown to be specifically associated with E1 or E2 (Sato et al, 1993). Complex glycans associated with glycoproteins on released virions would suggest transit through the trans Golgi and movement of virions through the host secretory pathway. If this suggestion is correct, intracellular sequestration of HCV glycoproteins and virion formation might then play a role in the establishment of chronic infections by minimizing immune surveillance and preventing lysis of virus-infected cells via antibody and complement.

Genetic variability. As for all positive-strand RNA viruses, the RNA-dependent RNA polymerase of HCV (NS5B) is believed to lack a 3'-5' exonuclease proof reading activity for removal of misincorporated bases. Replication is therefore error-prone leading to a "quasispecies" virus population consisting of a large number of variants (Martell et al, 1992; Martell et al, 1994). This variability is apparent at multiple levels. First, in a chronically infected individual changes in the virus population occur over time (Ogata et al, 1991; Okamoto et al, 1992) and these changes may have important consequences for disease. A particularly interesting example is the N-terminal 30 residues of the E2 glycoprotein which exhibits a much higher degree of variability than the rest of the polyprotein (for examples, see Higashi et al, 1993; Hijikata et al, 1991; Weiner et al, 1991). There is accumulating evidence that this hypervariable region, perhaps analogous to the V3 domain of HIV-1 gp120, may be under immune selection by circulating antiviral antibodies (Kato et al, 1993; Taniguchi et al, 1993; Weiner et al, 1992). In this model, antibodies directed against this portion of E2 may contribute to virus neutralization and thus drive the selection of variants with substitutions which escape neutralization. This plasticity suggests that a specific amino acid sequence in the E2 hypervariable region is not essential for other functions of the protein such as virion attachment, penetration, or assembly. Genetic variability may also contribute to the spectrum of different responses observed after treatment of chronically infected patients with alpha IFN. Diminished serum ALT levels and improved liver histology, which is sometimes correlated with a decrease in the level of circulating HCV RNA, is seen in only ~40% of those treated (Greiser-Wilke et al, 1991). After treatment, approximately 70% of the responders relapse. In some cases, after a transient loss of circulating viral RNA, renewed viremia is observed even during the course of treatment. While this might suggest the existence or generation of IFN-resistant HCV genotypes or variants, further work is needed to determine the relative contributions of virus genotype and host-specific differences in immune responsiveness. Finally, sequence comparisons of different HCV isolates around the world have uncovered enormous genetic diversity (reviewed in Ref. Bukh et al, 1995). Because biologically relevant serological assays such as cross-neutralization tests are lacking, HCV types (designated by numbers), subtypes (designated by letters), and isolates are currently being grouped on the basis of nucleotide or amino acid sequence similarity. Amino acid sequence similarity between the most divergent genotypes can be as little as ~50%, depending upon the protein being compared. This diversity is likely to have important biological implications, particularly for diagnostics, vaccine design, and therapy. As mentioned earlier, genotypes 1a and 1b are most common in the U.S. (see Bukh et al, 1995 for a discussion of genotype prevalence and distribution). Recently, in Yoo et al (1995) T7 transcripts from various derivatives of an HCV-1 cDNA clone were tested for their ability to replicate by transfection of the human hepatoma cell line, Huh7. Possible HCV replication was assessed by strand-specific RT/PCR (using 5' NTR primers) and metabolic labeling of HCV-specific RNAs with 3H-uridine. Transcripts terminating with either poly (A) or poly (U), were positive by these assays but those with a deletion of the 5' terminal 144 bases were not. In some cultures, HCV-specific RNA could be detected in the culture media and could be used to reinfect fresh Huh7 cells. While these claims cannot be directly refuted, it seems likely that the authors are not actually detecting authentic HCV replication. For instance, the authors' positive control was productive transfection of Huh7 cells with RNA extracted from 1 ml of high HCV titer chimpanzee plasma. This extracted sample would contain a maximum of 107 potentially infectious full-length HCV RNA molecules. Under optimum transfection conditions (other than microinjection), >105 RNA molecules of virion RNA (at least for poliovirus, Sindbis virus, or YF) are typically required to initiate a single infectious event. This suggests that in the HCV-1 experiment fewer than 100 cells would be productively transfected. At 16 days post-transfection, both positive- and negative-strand RNAs were readily detected after 8 hours of metabolic labeling. The detection of negative-strand RNA by this method (both for transfected virion RNA and transcript RNA) suggests that HCV is capable of both efficient replication and spread, and that the level of HCV RNA synthesis is similar to that which would be expected for a more robust flavivirus, such as YF (at the peak of a high multiplicity infection). However, despite numerous attempts, the authors were unable to detect HCV antigens in these cells using a variety of antisera or full-length positive- or negative-strands by Northern analysis (which is much more sensitive than metabolic labeling with 3H-uridine) (J. Han, personal communication). To say the least, these results are perplexing and not easily reconciled with authentic HCV replication. Finally, the critical experiment, demonstrating that RNA or virus derived from the HCV-1 clone is infectious in the chimpanzee model, has not been reported (despite the initial presentation of this work at a meeting more than two years ago). Work in other RNA virus systems has shown that specific terminal sequences can be critical for the generation of functional, replication competent RNAs (reviewed in Boyer and Haenni, 1994). Such sequences are believed to be involved in initiation of negative- and positive-strand RNA synthesis. In some cases, a few additional bases, or even longer non-viral sequences, are tolerated at the 5' and 3' termini; these sequences are typically lost or selected against during authentic viral replication. For other RNA viruses, extra bases, particularly at the 5' terminus, are deleterious (Boyer and Haenni, 1994). In contrast, except in a few cases, transcripts lacking authentic terminal sequences are non-functional (Boyer and Haenni, 1994). For instance, deletion of the 3' terminal secondary structure or conserved sequence elements in the 3' NTR of flavivirus genome RNA is lethal for YF (P. J. Bredenbeek and C.M.R., unpublished) or TBE (C. Mandl, personal communication) RNA replication. Given the importance of these sequence elements for other viruses, it is clear that a more rigorous determination of the HCV terminal sequences needed to be made.

SUMMARY OF THE INVENTION

In view of the aforementioned deficiencies attendant with prior art HCV cDNA clones and cell culture systems for the analysis of HCV replication, and for the development of therapeutic compositions therefor, it is evident that there exists a need in the art for identification of particularly the 3' terminal sequence of HCV which can be incorporated into a full-length cDNA clone capable of yielding infectious RNA transcripts, which then can be used as target sequences for the production of attenuated HCV for vaccines, and which can be used as targets for therapeutic compositions.

In accordance with the present invention, nucleotide sequences derived from cloned cDNA are provided which encode an HCV 3' terminal RNA element. The newly discovered 3' element in particular is highly conserved among HCV genotypes, and is a general feature of the HCV RNA genome.

The present invention includes a poly (UC) tract followed by a 101 nucleotide 3' terminal RNA sequence element, and to full-length HCV viral genome RNA or derived HCV RNA replicons containing the following sequence:
5'-poly (UC)-AAUGGUGGCUCCAUCUUAGC CCUAGUCACGGCUAGCUGUGAAAGGUC CGUGAGCCGCAUGACUGCAGAGAGUGC UGAUACUGGCCUCUCUGCWGAUCAUGU-3' (SEQ ID NO:1).

The present invention also relates to the complement of this RNA sequence and to full-length HCV negative-sense RNAs containing the following sequence:
5'-ACAUGAUCWGCAGAGAGGCCAGUAUCAGCA CUCUCUGCAGUCAUGCGG CUCACGGACCUUU- CACAGCUAGCCGUGACUAGGGCUAA- GAUGGAGCCA CCAUU-poly (GA)-3' (SEQ ID NO:2).

The present invention also relates to the DNA sequence corresponding to the 3' NTR element in the positive-sense HCV genome RNA:
5'-poly-(TC)-AATGGTGGCTCCATCTTAGCCCTAGT CACGGCTAGCTGTGAAAGGTCCGT GAGCCGCAT- GACTGCAGAGAGTGCTGATACTGGC- CTCTCTGCWGATCATG T-3' (SEQ ID NO:3).

The present invention also relates to the DNA sequence corresponding to the complement of the 3' NTR element present in negative-sense HCV RNA:
5'-ACATGATCWGCAGAGAGGCCAGTATCAGCACTC TCTGCAGTCATGCGGCTCACGGACCTTTCACAG CTAGCCGTGACTAGGGCTAAGATGGAGCCACCA TT-poly (GA)-3' (SEQ ID NO:4).

It should be appreciated, that although this sequence appears to "noncoding," it is possible that the sequence encodes a polypeptide of importance for HCV replication. There are two short open reading frames in the complement of the 3' terminal element which would be at the 5' of the negative-sense RNA followed by poly (A). These sequences could be expressed via translation of the negative strand RNA (either a full-length negative-strand or a subgenomic RNA).

In a further embodiment, this element, which extends beyond the previously accepted homopolymer tracts of poly(U) or poly(A), can be used to assemble full-length HCV cDNA clones for HCV-H and other HCV isolates (genotypes, types and subtypes) (HCV-1 acc.#M62321; HC-J1 acc.#D10749; HC-J acc.#D90208; HCV-BK acc.#M58335; HCV-H acc.#M67463, HC-J6 acc.#D00944, HC-J8 acc.#D01221; HC-J483 acc.#D13558; HC-J491 acc.#D10750; HC-C2 acc.#D10934; HCV-JK acc.#X61596; HCV-N acc.#S62220; HCV-T acc.#M84745; HCV-JT acc.#D01171; HCV-JT acc.#D01172; HC-G9 acc.#D14853; HCV-K3a acc.#D28917; NZL1 acc.#D17763; HCV-Tr acc.#D26556). Such full-length viruses or derived HCV RNA replicons are ueful for the study of HCV replication and virus-host interactions as well as for the development of screening assays for HCV therapeutics and the evaluation of therapeutic compounds.

In a still further embodiment, live-attenuated strains of HCV are provided for use as vaccines.

The present invention also relates to a recombinant DNA or RNA molecule or a degenerate variant thereof, which encodes the 3' HCV terminal sequence element; preferably the nucleic acid contains a sequence with substantially the same nucleotide sequence as SEQ ID NOS:1–4 or that shown in FIG. 3 (SEQ ID NOS:20–24; the parts of sequences downstream of the poly (U) tract only), FIG. 6 (SEQ ID NOS:28–31) and FIG. 8 (SEQ ID NOS:33–36) and sequences forming a secondary structure similar to that of FIG. 4 (SEQ ID NO:25), or alternatively, a structure which may be formed via interaction of the 3' terminal sequence element (or its compliment) with other HCV RNA sequences (e.g., 5' terminal sequences or other sequences at or near the 3' NTR).

The sequences of the HCV of the present invention or portions thereof, may be prepared as probes (or primers for RT-PCR) to screen for complementary sequences and related clones in the same or alternate species. The present invention extends to probes or primers so prepared that may be provided for screening cDNA libraries, plasma or infected cells for HCV. For example, the probes may be prepared synthetically and by recombinant DNA with a variety of known vectors, such as the phage, plasmid or viral vector. The present invention also includes the preparation of plasmids including such vectors, and the use of the DNA/RNA sequences to construct vectors expressing anti-sense RNA or ribozymes which would attack natural or engineered HCV RNAs containing any or all of the sequences set forth in FIGS. 3 (SEQ ID NOS:20–24), FIG. 6 (SEQ ID NOS:28–31) and FIG. 8 (SEQ ID NOS:33–36) or as above as SEQ ID NOS:1–4, derivatives of the sequences, or homologous sequences from other HCV types/subtypes. Correspondingly, the preparation of anti-sense RNA and ribozymes are included herein.

The present invention also includes RNA molecules having the properties noted herein, and that display the sequences set forth above and described above and selected from SEQ ID NOS:1–4, 20–24, 28–31 and 33–36.

In a further embodiment of the invention, the full nucleotide sequence of the HCV containing the above determined sequences may be introduced into an appropriate host. The invention accordingly extends to host cells transfected or transformed with the cloned HCV sequences and/or RNA derived therefrom, and more particularly, replication competent and/or complete DNA/RNA sequences assembled using the sequences, or homologous derivatives set forth above.

According to other preferred features of certain preferred embodiments of the present invention, a transiently transfected or stable cell line is provided to produce infectious HCV, and attenuated strains of HCV.

The present invention naturally contemplates several means for preparation of the HCV sequences, including as illustrated herein known recombinant techniques, and the invention is accordingly intended to cover such synthetic preparations within its scope. The isolation of the sequences disclosed herein facilitates the reproduction of not only the nucleic acid sequences themselves, but also infectious HCV, and attenuated HCV by such recombinant techniques, and accordingly, the invention extends to the wild type and attenuated HCVs so prepared from the disclosed sequences, and to transiently transfected cells or stable cell lines expressing this sequence, replicating HCV RNA, and/or producing virus.

The invention includes an assay system for screening of potential drugs effective to modulate replication of HCV in target cells by interrupting or potentiating the viral life cycle. Potentiation would be desirable where stocks of HCV were to be produced, for use in experimental as well as therapeutic regimes (i.e., vaccines). In one instance, the test drug could be administered to a cellular sample transfected with an infectious HCV, cDNA clone or replication-competent RNA, to determine its effect upon the replicative activity of the HCV in the presence of any chemical sample (including DNA or RNA), or to the test drug, by comparison with a control.

The assay system could more importantly be adapted to identify drugs or other entities that are capable of binding to the HCV RNA sequences or which bind essential factors interacting with these sequences, thereby inhibiting or potentiating replication. Such assays would be useful in the development of drugs that would be specific against a wide range of HCV isolates, due to the conservation of an important 3' terminal sequence motif, identified by SEQ ID NOS:1–4.

In yet a further embodiment, the invention contemplates antagonists of the activity of HCV, in particular, an agent or molecule that inhibits viral replication or transcriptional activity in general. In a specific embodiment, the antagonist can be an oligonucleotide having the sequence (or its complement) of a portion of a 3' terminal domain of an HCV. Such oligonucleotides may be capable of disrupting strand synthesis required for viral replication, translation of HCV RNA into protein, or packaging of genome RNA into virus particles.

The diagnostic utility of the present invention extends to the use of the present 3' terminal sequence in assays to screen for HCV infection. In particular, probes or PCR primers may be produced which are capable of detecting HCV infection in blood, or in infected cells. Such probes may be labelled with any detectable label. In the instance where a radioactive label, such as the isotopes $^3H$, $^{14}C$, $^{32}P$, 35S, $^{36}Cl$, $^{51}Cr$, $^{57}Co$, $^{58}Co$, $^{59}Fe$, $^{90}I$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention includes an assay system which may be prepared in the form of a test kit for the quantitative analysis of the extent of the presence of the HCV sequences, or to identify drugs or other agents that may mimic or block the activity of such sequences. The system or test kit may comprise a labeled component prepared by one of the radioactive and/or enzymatic techniques discussed herein, coupling a label to a probe for HCV nucleic acid, or a binding partner thereof, or a binding partner of the HCV virion itself, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the HCV sequences(s), or active fragments thereof, or upon agents or other drugs determined to possess the same activity. A first therapeutic method is associated with the prevention of infection by HCV, in particular by providing a vaccine composed of an attenuated HCV, designed by mutating the sequence elements disclosed herein.

More specifically, the therapeutic method generally referred to herein could include the method for the treatment of hepatitis or other cellular dysfunctions caused by HCV by the administration of pharmaceutical compositions that may comprise effective inhibitors of the HCV or its subunits, or other equally effective drugs developed for instance by a drug screening assay prepared and used in accordance with a further aspect of the present invention. For example, drugs or other binding partners to the HCV nucleic acid or its encoded proteins, may be administered to inhibit or potentiate transcriptional activity.

In particular, HSV or its herein-identified 3' sequence element or fragments thereof, and binding partners thereto could be prepared in pharmaceutical formulations for administration in instances wherein interferon therapy is appropriate, such as to treat chronic viral hepatitis or other HCV-associated illnesses.

Accordingly, it is a principal object of the present invention to provide a novel 3' sequence element of HCV, as well as full-length HCV genomes which encode wild-type or attenuated HCV bearing this additional sequence.

It is a further object of the present invention to provide a method for detecting the presence of the HCV in mammals in which HCV is suspected to be present.

It is a further object of the present invention to provide a method and associated assay system for screening substances such as drugs, agents and the like, potentially effective in combating the adverse effects of the HCV in mammals.

It is a still further object of the present invention to provide a method for the treatment of mammals to control the amount or activity of the HCV or fragments thereof, so as to alter the adverse consequences of such presence or activity.

It is a still further object of the present invention to provide a method for the treatment of mammals to control the amount or activity of the HCV or its subunits, so as to treat or avert the adverse consequences of a pathological state.

It is a still further object of the present invention to provide pharmaceutical compositions for use in therapeutic methods which comprise or are based upon the HCV, its sequence elements, their binding partner(s), or upon agents or drugs that control the production, or that mimic or antagonize the activities of the HCV.

Other objects and advantages will become apparent to those skilled in the art from a review of the ensuing description which proceeds with reference to the following illustrative drawings.

BRIEF DESCRIPTION OF THE DRAWINGS

FIG. 1 depicts a method for determining the 3' terminal sequence of HCV. A phosphorylated synthetic oligodeoxynucleotide ("oligo A"; 5'-GACTGTTGTGGCCTGCAGGGCCGAATT-3'; SEQ ID NO:5) was ligated to the 3' end of the RNA to serve as a specific priming site for cDNA synthesis. A primer for cDNA synthesis ("oligo B";(1)5-TTGAATTCGACCCTGCAGGCCACAACA-3'; SEQ ID NO:6 or B(2); 5'-TTGAATTCGGCCCTGCAGGCCACAACAGTC-3'; SEQ ID NO:7) was complementary to that used for ligation to the RNA; a second positive-sense primer for PCR corresponded to a sequence near the 3' end of the HCV ORF ("oligo C"; 5'-CAAGTCGACGGGGAGACATTTATCACAGC-3'; SEQ ID NO:8).

FIG. 2 depicts an alignment comparing the portion of the 3' terminal sequence (DNA corresponding to the positive sense HCV genome RNA) of HCV-H-AAK [SEQ ID NO:11; determined by sequencing of an uncloned DNA fragment which was synthesized by PCR using an oligo (dA) primer and "oligo C"] between the termination codon of the ORF and the poly (U) tract with a partial list of published sequences for other HCV isolates (genotypes): HCV-H(1a) isolate (SEQ ID NO:9); HCV-1(1a) (SEQ ID NO:10); HCV-J1(1a) (SEQ ID NO:12); HCV-BK(1b) (SEQ ID NO:13); HCV-TW(1b) (SEQ ID NO:14); HCV-N(1b) (SEQ ID NO:15); HCV-J6(2a) (SEQ ID NO:16); HCV-J8 (SEQ ID NO:17); HCV-NZL1(3a) (SEQ ID NO:18); and HCV-Tr(3b) (SEQ ID NO:19).

FIG. 3 depicts the sequence (DNA corresponding to the positive sense HCV genome RNA) of HCV-H 3' clones including H77-#1,2 (SEQ ID NO:20), H77-#8 (SEQ ID NO:21), H77-#10 (SEQ ID NO:22), H77-#74 (SEQ ID NO:23), H77-#5 (SEQ ID NO:24).

Figure 5:
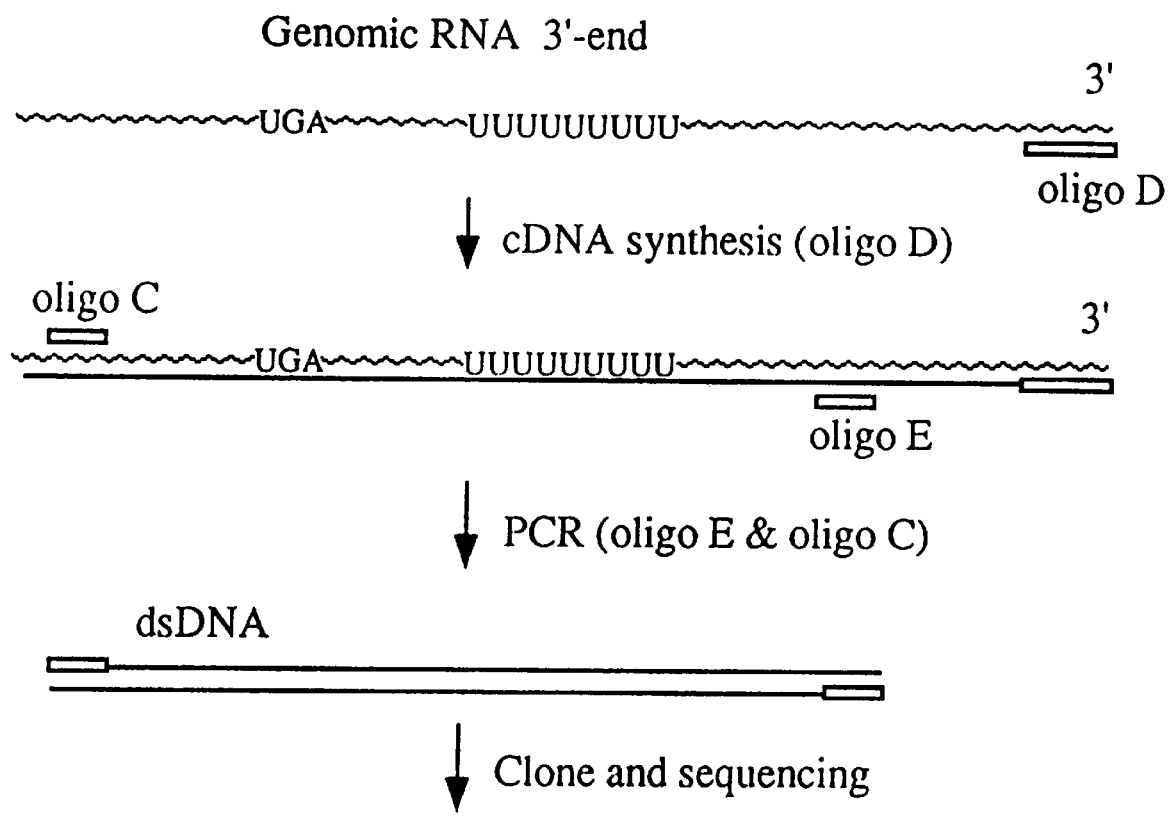

FIG. 5 depicts the scheme used for the RT/PCR amplification and cloning of partial 3' terminal segments from four different HCV subtypes (1b, 3, 4 and 4a) (SEQ ID NOS:28–31). Briefly, oligo D (5'-TAACATGATCAGCAGAGAGGCCAG-3') (SEQ ID NO:26) was annealed to the 3' end of the genomic RNA, and cDNA was synthesized. Next, PCR was performed using oligo C (SEQ ID NO:8) and oligo E (5'-CTCACGGACCTTTCACAGC-3') (SEQ ID NO:27). The PCR products were cloned and sequenced.

FIG. 6 shows an alignment of sequences (5'–3') (DNA sequence corresponding to the positive-sense HCV genome RNA) determined for 3 segments from HCV subtypes 1b, 3, 4 and 4a (SEQ ID NOS:28–31) amplified and cloned as described in FIG. 5. The termination codon (TGA) is shown in bold.

Figure 7:
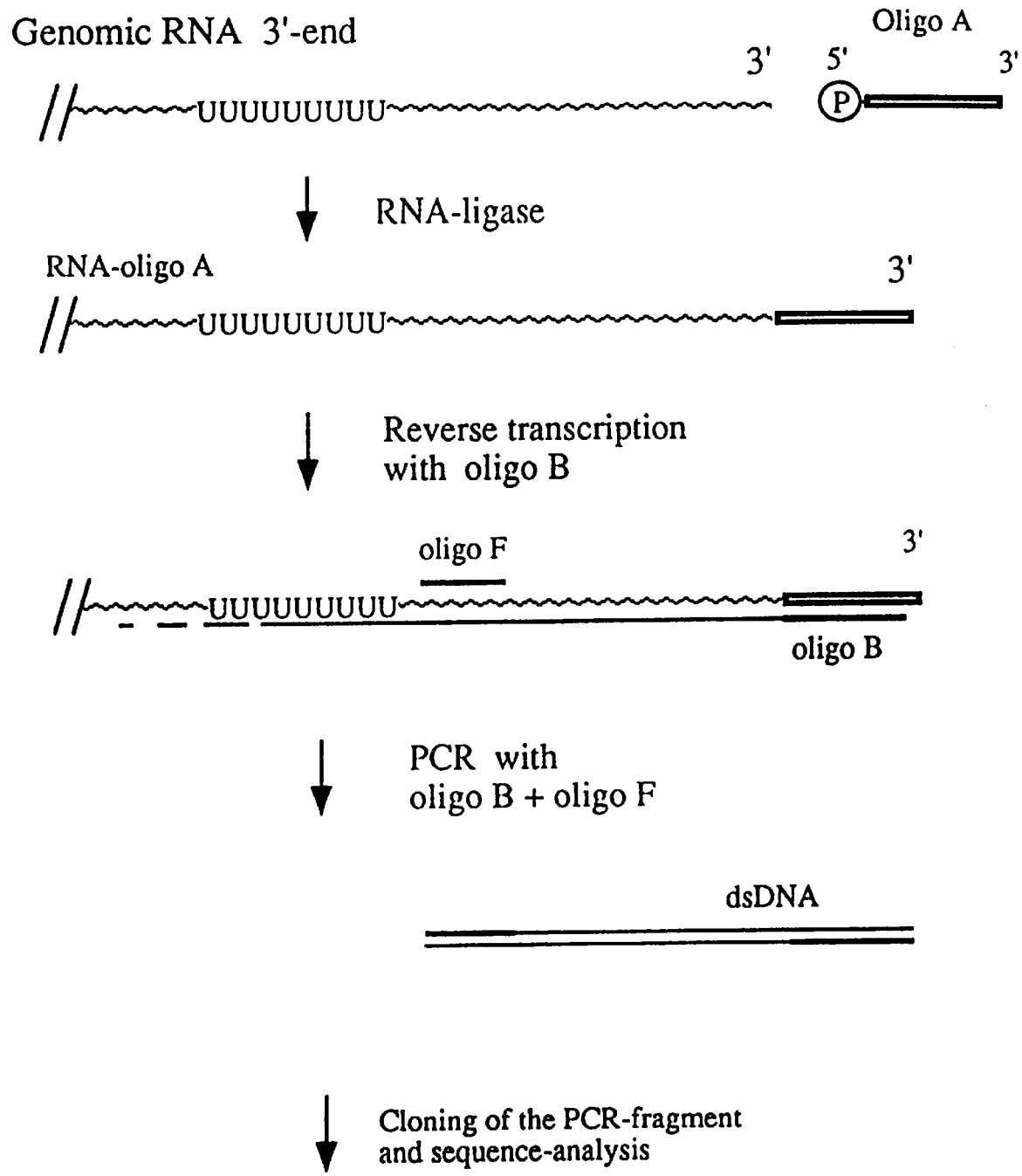

FIG. 7 depicts a scheme for 3' end oligonucleotide ligation, RT/PCR and cloning of the HCV RNA from four different HCV genotypes/subtypes (1b, 3, 4 and 4a). Methods were essentially as outline in FIG. 1, except that oligo F (5'-CCAAGAATTCCCTAGTCACGGCTAGC-3') (SEQ ID NO:32) was used instead of oligo C.

FIG. 8 shows the sequences (DNA sequence corresponding to the positive-sense HCV genome RNA) (SEQ ID NOS:33–36) resulting from the analysis described in FIG. 7. Isolate-specific sequence differences are shown in bold.

Figure 9:
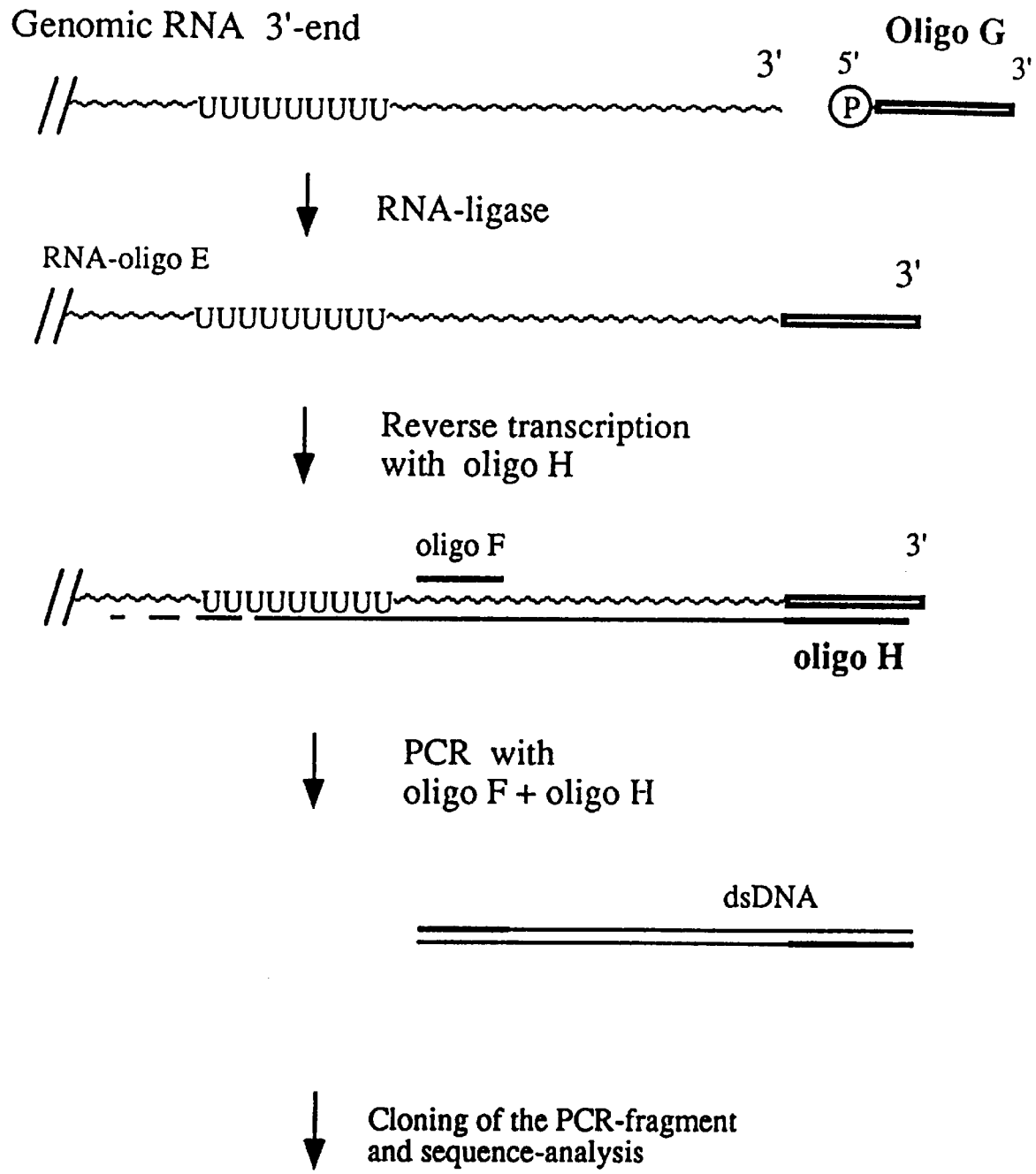

FIG. 9 depicts a scheme for alternative 3' end primer ligation and RT/PCR for a genotype 4 isolate of HCV. A different oligonucleotide ("oligo G"; 5'-CGCACCCTGTCCGACTACAACATCC-3'; SEQ ID NO:37) was used for the RNA ligation step. Primers used for cDNA synthesis ("oligo H"; CAGAATTCTTGTAGTCGGACAGGGTGCG-3'; SEQ ID NO:38) and for PCR ("oligo F" and "oligo H") are indicated.

Figure 10:
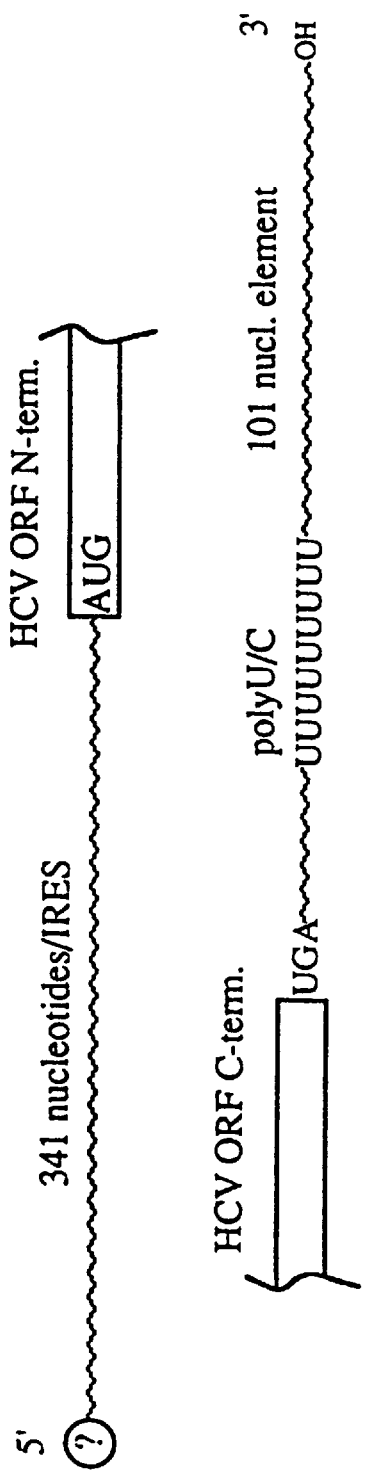

FIG. 10 depicts the predicted structure of a full-length HCV genome RNA (precise numbers refer to HCV-H). The genome RNA probably initiates with a G residue and contains a 5' non-traiislated region (NTR) of 341 bases. The ORF consists of 9033 bases encoding a polyprotein of 3011 amino acid residues. Following the opal (UGA) stop codon is a sequence of 40 bases, a poly (U) tract, a polypyrimidine stretch, and a novel conserved RNA element of 101 bases.

DETAILED DESCRIPTION

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing hierein, the following terms shall have the definitions set out below.

The terms "3' terminal sequence element," "3' terminus," "3' sequence element," and any variants not specifically listed, may be used herein interchangeably, and as used throughout the present application and claims refer to nucleotide sequences having the sequence data described herein and presented in SEQ ID NOS:1–4 or that shown FIG. 3 (SEQ ID NOS:20–24; the parts of sequences downstream of the poly (U) tract only), FIG. 6 (SEQ ID NOS:28–31) and FIG. 8 (SEQ ID NOS:33–36) and the profile of properties set forth herein and in the Claims. It should be appreciated that the terms "3' terminal sequence element," "3' terminus," "3' sequence element," are meant to encompass all of the following sequences: (i) an RNA sequence at the 3' terminus of the positive-sense genome RNA; (ii) the complement of this RNA sequence at the 5' terminus of the HCV negative-sense RNA; (iii) the DNA sequence corresponding to the positive-sense sequence of the RNA element; and (iv) the DNA sequence corresponding to the negative-sense sequence of the RNA element. Examples of such sequences are illustrated in SEQ ID NOS:1–4, respectively. Accordingly, nucleotide sequences displaying substantially equivalent or altered properties are likewise contemplated. These modifications may be deliberate, for example, such as modifications obtained through site-directed mutagenesis, or may be accidental, such as those obtained through mutations in hosts that are producers of the complex or its named subunits. Also, the terms "3' terminal sequence," "3' terminus," and "3' sequence element," are intended to include within their scope nucleic acid molecules specifically recited herein as well as all substantially homologous analogs and allelic variations.

Any amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA or RNA replication in vivo; i.e., capable of replication under its own control. Bradenbeck and Rice (1992) *Semin. Virol.* 3:297–310 contains a description of RNA replicons.

A "vector" is a replicon, such as a plasmid, phage or cosmid, to which another DNA (or RNA) segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "RNA molecule" refers to the polymeric form of ribonucleotides (adenine, guanine, uridine, or cytosine) in its either single stranded for, or a double-stranded helix. This term refers only to the primary and secondary structure o the molecule, and does not limit it to any particular tertiary forms. Thus, this term includes single-stranded and double-stranded RNA found, inter alia, in linear or circular RNA molecules. In discussing the structure of particular RNA molecules, sequence may be described herein according to the normal convention of giving the sequence in the 5' to 3' direction.

An "origin of replication" refers to those DNA sequences that participate in DNA synthesis.

A "coding sequence" or "open reading framen" is a nucleotide sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA or RNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences. Promoter sequences can also be used to refer to analogous RNA sequences or structures of similar function in RNA virus replication and transcription.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. RNA sequences can also serve as expression control sequences by virtue of their ability to modulate translation, RNA stability, and replication (for RNA viruses).

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. This definition can be applied to RNA molecules which can be used to transform or "transfect" cells. For some RNA viruses, such methods can be used to produce infected cell lines which transiently or continuously support virus replication and, in some cases, which produce infectious viral particles.

Two DNA or RNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al, supra; DNA Cloning, Vols. I & II, supra; Nucleic Acid Hybridization, supra. More distantly related sequences or structures, which may have the same or similar functions, are referred to as "homologous." In the extreme case, such sequences could be unrelated in terms of linear sequence identity, but may have substantially similar secondary structure.

A "heterologous" region of a DNA or RNA construct is an identifiable segment of DNA or RNA molecule within a larger nucleic acid that is not found in association with the larger molecule in nature. For instance, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunloglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG or AUG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" in general refers to salt and temperature conditions substantially equivalent to 5× SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10°–20° C. below the predicted or determined $T_m$ with washes of higher stringency, if desired.

By "HCV" is meant a diverse group of related viruses classified as a separate genus in the flavivirus family. The characteristics of this genus are described in the Background of the Invention above, and include such members as HCV-1, HC-J1, HC-J, HCV-BK, HCV-H, HC-J6, HC-J8, HC-J483, HC-J491, HC-C2, HCV-JK, HCV-N, HCV-T, HCV-JT, HC-G9, HCV-K3a, NZL1, HCV-Tr and the like.

In its primary aspect, the present invention concerns the identification of novel terminal sequences present in HCV positive-sense genomic RNA.

In a particular embodiment, the present invention relates to novel 5' and 3' terminal sequences which are highly conserved by all members of the herein disclosed HCVs.

As stated above, the present invention also relates to a recombinant DNA or RNA molecule or cloned gene, or a degenerate variant thereof, which encodes an HCV, or a fragment thereof, which has a nucleotide sequence or is complementary to a nucleotide sequence shown in SEQ ID NOS:1–4 or that shown FIG. 3 (SEQ ID NOS:20–24; the parts of sequences downstream of the poly (U) tract only), FIG. 6 (SEQ ID NOS:28–31) and FIG. 8 (SEQ ID NOS:33–36).

The invention also relates to infectious HCV cDNA clones comprising previously disclosed 5' non-coding, coding and 3' non-coding sequences including those encoding poly (U) or poly (A) tracts ((HCV-1 acc.#M62321; HC-J1 acc.#D10749; HC-J acc.#D90208; HCV-BK acc.#M58335; HCV-H acc.#M67463; HC-J6 acc.#D00944; HC-J8 acc.#D01221; HC-J483 acc.#D13558; HC-J491 acc.#D10750; HC-C2 acc.#D10934; HCV-JK acc.#X61596; HCV-N acc.#S62220; HCV-T acc.#M84745; HCV-JT acc.#D0171; HCV-JT acc.#D01172; HC-G9 acc.#D14853; HCV-K3a acc.#D28917; NZL1 acc.#D17763; HCV-Tr acc.#D26556 and others), the polypyrimidine tract, and the novel 3' element of 101 bases (SEQ ID NO:1c, d or related sequences).

The possibilities both diagnostic and therapeutic that are raised by the existence of the full length HCV clone, derive from the fact that the terminal sequences of viral genomes can be critical for the generation of functional, replication competent RNAs (Boyer et al, *J. Gen. Virol.* 198:415–426). As suggested earlier and elaborated further on herein, the present invention contemplates pharmaceutical intervention in the infectious life cycle of HCV.

Thus, in instances where it is desired to inhibit infectivity of HCV, an appropriate inhibitor of the 3' sequence element could be introduced to block the interaction of the initiation of negative- and positive-strand synthesis required for viral replication. Correspondingly, infectivity may be remedied by the introduction of additional quantities of a nucleic acid molecule encoding the 3' sequence element or its chemical or pharmaceutical cognates, analogs, fragments and the like.

As discussed earlier, the molecules or agents exhibiting either mimicry or antagonism to the 3' sequence element, or control over the replication of the HCV, may be prepared in pharmaceutical compositions, with a suitable carrier and at a strength effective for administration by various means to a patient experiencing an adverse medical condition associated with HCV for the treatment thereof. A variety of administrative techniques may be utilized, among them parenteral techniques such as subcutaneous, intravenous and intraperitoneal injections, catheterizations and the like. Average quantities of the molecules or their subunits may vary and in particular should be based upon the recommendations and prescription of a qualified physician or veterinarian.

As suggested earlier, the diagnostic method of the present invention comprises examining a cellular sample or medium by means of an assay including an effective amount of a binding partner to the HCV RNA. As previously discussed, patients capable of benefiting from this method include those suffering from infection by HCV. Methods for isolating the molecules which bind HCV sequences to assist in the examination of the target cells are all well-known in the art.

The present invention further contemplates therapeutic compositions useful in practicing the therapeutic methods of this invention. A subject therapeutic composition includes, in admixture, a pharmaceutically acceptable excipient (carrier) and one or more of a 3' terminal sequence element, analog thereof or fragment thereof, or a molecule which inhibits the properties or activities of that sequence element, as described herein as an active ingredient. In a preferred embodiment, the composition comprises a molecule capable of modulating the secondary structure formation of the 3' terminus of the HCV RNA, and/or the initiation of negative- and positive-strand RNA synthesis and/or RNA packaging.

A further therapeutic composition includes a full-length attenuated HCV which can be used as a vaccine against HCV infection, wherein a sequence within the genome of HCV, in particular the 3' terminal sequence element (SEQ ID NOS:1–4) has been modified, either as a naturally-occurring isolate, or via in vitro evaluation or site-directed mutagenesis. Particular mutations suitable for such attenuated viruses include those which alter the structure of the 3' terminus of the HCV genome RNA (or the 5' terminus of negative sense HCV RNA), and, by so doing, alter the initiation and/or translation of negative- and positive-strand RNA synthesis and/or RNA packaging. Such modifications may be aided by computer modelling and evaluated using infectivity assays.

The preparation of therapeutic compositions which contain the 3' terminal sequence element or antagonist thereof, or the full-length attenuated HCV, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of HCV desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. In the case of attenuated virus used as a vaccine, dosages could range from 10 to $10^6$ infectious doses. For inactivated viral vaccines, higher doses of HCV antigen and a suitable adjuvant could be required. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the 3' sequence element, its antagonist, or analog thereof, in combination with an antibiotic, a steroid, interferon or other anti-HCV therapeutic. Exemplary formulations are given below:

| Formulations | |
|---|---|
| Ingredient | mg/ml |
| Intravenous Formulation I | |
| cefotaxime | 250.0 |
| HCV, fragment or antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| HCV, fragment or antagonist | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| HCV, fragment or antagonist | 10.0 |
| sodium bisulfite USP | 3.2 |
| disodium edetate USP | 0.1 |
| water for injection q.s.a.d. | 1.0 ml |
| Intravenous Formulation IV | |
| HCV, fragment or antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| HCV, fragment or antagonist | 5.0 |
| sodium bisulfite USP | 3.2 |
| disodium edetate USP | 0.1 |
| water for injection q.s.a.d. | 1.0 ml |

As used herein, "pg" means picogram, "ing" means nanogram, "ug" or "$\mu$g" mean microgram, "mg" means milligram, "ul" or "$\mu$l" mean microliter, "ml" means milliliter, "l" means liter.

A wide variety of cell types may be useful as host cells for HCV replication, as initiated using the functional HCV cDNA clones created by incorporation of sequences from the present invention. These host cells may include primary human cells (e.g., hepatocytes, T-cells, B-cells, monocytes/macrophages, foreskin fibroblasts) as well as continuous human cell lines [e.g., HepG2, Huh7, HUT78, HPB-Ma, MT-2 (and other HTLV-I and HTLV-II infected T-cell lines), Namalowa, Daudi, EBV-transformed LCLs]. In addition, continuous cell lines which are readily transfected with RNA and permissive for replication of flaviviruses or pestiviruses may support HCV replication (e.g. SW-13, Vero, BHK-21, COS, PK-15, MBCK). One skilled in the art will be able to select the proper host cells without undue experimentation to accomplish the desired infectivity assay without departing for the scope of this invention.

It is further intended that 3' terminal sequence analogs or HCV analogs may be prepared from nucleotide sequences derived within the scope of the present invention. Analogs, such as fragments or mutants (e.g., "muteins,") can be produced by standard cleavage by restriction enzymes, or site-directed mutagenesis of the HCV coding and noncoding (5' and 3' terminal) sequences. Analogs exhibiting "HCV inhibiting activity" such as small molecules, whether functioning as promoters or inhibitors, may be identified by known in vivo and/or in vitro assays.

As mentioned above, a DNA sequence encoding the 3' sequence element, its complement, or the full length wild-type or attenuated HCV can be prepared synthetically rather than cloned. The DNA sequence can be designed with the appropriate codons for amino acid sequence encoded by the HCV open reading frame. The complete sequence is assembled from overlapping oligonucleotides prepared by standard methods and assembled into a complete coding sequence. See, e.g., Edge, *Nature*, 292:756 (1981); Nambair et al, *Science*, 223:1299 (1984); Jay et al, *J. Biol. Chem.*, 259:6311 (1984).

The ability of the 3' terminal sequence element to drive replication-competent HCV RNAs can be analyzed by using constructs in which the ORF of HCV has been replaced by a reporter gene, such as luciferase, which can be detected directly and correlated to the level of HCV RNA in the cell. In particular, the 3' terminal sequence element can be used to derive replication competent HCV RNAs, either full-length RNAs capable of complete replication and virus production or replicons. Such replicons would be capable of RNA replication, but might lack the structural region/packaging machinery and hence not produce virus. Cells transfected/transformed with such replicons (containing the 3' element) would be useful for inhibitors of HCV RNA replication, including those which might interfere with the function of the 3' element or its complement. RNA replication could be assessed either by looking directly at HCV RNA levels (RT/PCR, B-DNA, Northern blot analyses) or by incorporating a sensitive reporter (like luciferase) under the control of the HCV RNA replication and translational machinery.

Synthetic DNA sequences allow convenient construction of genes which will express HCV, HCV variants or attenuated HCV. Alternatively, DNA encoding variant or attenuated HCV can be made by site-directed mutagenesis of native HCV cDNAs.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create HCV virions containing proteins with unnatural amino acids.

The present invention extends to the preparation of antisense nucleotides and ribozymes that may be used to interfere with HCV RNA translation, stability, replication/transcription and/or packaging. This approach utilizes antisense nucleic acid and ribozymes to block viral replication, either by masking the HCV RNA with an antisense nucleic acid or cleaving it with a ribozyme.

Antisense nucleic acids are DNA or RNA molecules that are complementary to at least a portion of a specific RNA molecule. (See Weintraub, 1990; Marcus-Sekura, 1988.) In the cell, they hybridize to that RNA, forming a double stranded molecule. Therefore, antisense nucleic acids may interfere with viral replication (either by a direct blocking effect or by leading to degradation of the target RNA by cellular enzymes). Oligomers of about fifteen nucleotides are appropriate, since they are easy to synthesize and are likely to pose fewer problems than larger molecules when introducing them into HCV-infectible cells. However, also suitable are oligonucleotides of natural structure or those with modifications to enhance stability, facilitate, uptake, etc. In addition, longer antisense RNAs can be generated in vivo in hepatocytes or other HCV target cells using gene therapy approaches. Antisense methods have been used to inhibit the expression of many genes in vitro (Marcus-Sekura, 1988; Hambor et al, 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only RNAs (such as the HCV positive-sense genome RNA or its complement) with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave HCV RNA. It should be appreciated that such antisense molecules and ribozymes will encompass nucleotide sequences of both positive and negative strand polarity, such that they may bind to both the positive and negative strand HCV RNAs.

The present invention also relates to a variety of diagnostic applications, including methods for detecting HCV. The invention also relates to methods of correlating 3' NTR sequences with various clinical parameters such as disease severity, response to treatment with interferon, and immune status, or to determine tissue tropism (predictive diagnostics.)

The present HCV sequences can be used experimentally to identify HCV isolates containing additional 3' sequences, to determine 3' NTR sequences for various HCV genotypes to define further areas of conservation and divergence. Also, the chemical modification and analysis of the RNA by RNAse mapping and three-dimensional structure analysis of the RNA is an aid to identifying host or viral factors which interact with the sequence and/or identifying molecules which inhibit replication. HCV RNA can also be used therapeutically, i.e., attenuated HCV can be used for vaccine development, and the 3' NTR sequence element may be used as a trans-dominant inhibitor of HCV replication via gene therapy.

Replication of HCV in cells can be ascertained by branched DNA (B-DNA), quantitative RT/PCR and immunological procedures, or using standard methods for determining virus titer (i.e., titration in the chimpanzee). The procedures and their application are all familiar to those skilled in the art and accordingly may be utilized within the scope of the present invention. A "competitive" antibody binding procedure is described in U.S. Pat. Nos. 3,654,090 and 3,850,752. A "sandwich" procedure, is described in U.S. Pat. Nos. RE 31,006 and 4,016,043. Still other procedures are known such as the "double antibody", or "DASP" procedure.

In each instance, HCV proteins form complexes with one or more antibody(ies) or binding partners and one member of the complex is labeled with a detectable label. Alternatively, an antibody may be raised, or identified in HCV-infected patients, which binds to the present HCV 3' terminal sequence element. The fact that a complex has formed and, if desired, the amount thereof, can be determined by known methods applicable to the detection of labels.

Also within the scope of the invention are RNA molecules which mimic the 3' terminal sequence element or its complement or bind to these elements, selected in vitro using the "SELEX" (Tuerk and Gold, 19__) or other in vitro selection/evolution approaches. These methods provide libraries of RNAs with randomized sequences which can be selected by reiterative binding to a target (in this case, the 3' terminal sequence element, its complement, or the cognate binding partners required for the functions of these respective elements), and RNAs bound thereto are amplified by PCR. Such molecules may either mimic the structure of the 3' terminal element or be competitive inhibitors of the 3' terminal sequence element. Such SELEX RNAs may be suitable for diagnostic and even therapeutic uses within the scope of the present invention.

Alternatively, the presence of HCV RNA can be determined by Northern analysis, polymerase chain reaction (PCR), primer extension, and the like.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

An antibody to HCV proteins, or a probe for HCV RNA or their binding partner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, 90Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected probe by reaction with bridging molecules such as carbodiimides, diisocyanates, glutaraldehyde and the like. Many enzymes which can be used in these procedures are known and can be utilized. Those preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods. In addition, a probe may be biotin-labelled, and thereafter be detected with labelled avidin, or a combination of avidin and a labelled anti-avidin antibody. Probes may also have digoxygenin incorporated therein and be then detected with a labelled anti-digoxygenin and detected with a labelled anti-digoxygenin antibody.

In a further embodiment of this invention, commercial test kits suitable for use by a medical specialist may be prepared to determine the presence or absence of infectious HCV in suspected patient samples. Such test kits may employ techniques such as RT/PCR, branched DNA and ligation chain reaction (LCR). In accordance with the testing techniques discussed above, one class of such kits will contain at least a labeled HCV antibody or oligonucleotide probe or its binding partner, and directions, of course, depending upon the method selected. The kits may also contain peripheral reagents such as buffers, stabilizers, etc.

Accordingly, a test kit may be prepared for the demonstration of the presence of HCV, comprising:

(a) a predetermined amount of at least one labeled oligonucleotide probe directed to a 3' sequence element of the HCV genome, obtained by the direct or indirect attachment of the oligonucleotide or a specific binding partner thereto, to a detectable label;

(b) other reagents; and (c) directions for use of said kit.

More specifically, the diagnostic test kit may comprise:

(a) a known amount of the labeled oligonucleotide probe as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In accordance with the above, an assay system for screening potential drugs effective to modulate the replicative activity of the HCV RNA may be prepared. The infectious HCV RNA may be introduced into a test system, and the prospective drug may also be introduced into the resulting cell culture, and the culture thereafter examined to observe any changes in the replicative activity of the cells, due to the addition of the prospective drug.

PRELIMINARY CONSIDERATIONS

While a great deal of progress has been made in the last several years, there are still a vast number of unanswered questions concerning HCV replication, pathogenesis and immunity. The field is rapidly reaching a bottleneck some aspects of the functions of the HCV genome RNA and its encoded proteins are understood, but prior to the present invention, no way existed of experimentally testing structure/function questions in the context of authentic virus replication. Such analyses are critical for understanding each step in the virus life cycle at a level which will allows the design of protective vaccines and effective therapy for chronically infected patients.

The present invention stemmed from attempts to construct functional cDNA clones for HCV, in particular the HCV-H strain. Prior to the present invention, attempts to recover infectious HCV RNA from cDNA have been unsuccessful. Several possible explanations, alone or in combination, account for previous failures, including missing or incorrect terminal sequences, internal errors deleterious or lethal for HCV replication, or inadequate methods for assaying infectivity and replication.

Rationale for rigorously determining the HCV-H termini. 5' and 3' terminal sequences of HCV-H were previously unknown. Previous attempts to generate functional transcripts used terminal sequences determined for other HCV isolates. As mentioned above, work in other RNA virus systems has shown that specific terminal sequences can be critical for the generation of functional, replication competent RNAs (Boyer and Haenni, (1994) *J. Gen. Virol.* 198:415–426). Such sequences are believed to be involved in initiation of negative- and positive-strand RNA synthesis. Given the importance of these sequence elements for other viruses, the present invention more rigorously determined the HCV-H terminal sequences.

Structure of the 5' NTR. Methods used to amplify and clone the extreme 5' termini of RNAs include homopolymer tailing or ligation of synthetic oligonucleotides to first-strand cDNA (5' RACE), cyclization of first-strand cDNA followed by inverse PCR (Zeiner and Gehring (1994) *BioTechniques* 17:1051–1053), or cyclization of genome RNA with RNA ligase (after treatment to remove 5' cap structures, if necessary) followed by cDNA synthesis and PCR amplification across the 5'–3' junction (Mandl et al (1991) *Biotechniques* 10:486). 5' terminal sequences were determined for a number of HCV isolates and are in general agreement. For HCV-H, both the cyclization/inverse PCR and 5' RACE methods were used to determine a 5'-terminal consensus sequence:

5'-GCCAGCCCCCTGATGGGGGCGACACTCCACCAT GAAATC-3' (SEQ ID NO:39)

This sequence is highly homologous to those determined for other isolates. At lower frequency, clones with additional 5' residues (usually 1 additional G) were also recovered. Although this might reflect additional sequences or heterogeneity at the HCV 5' terminus, these clones may be artifactual and created by partial copying of a 5' cap structure or addition of non-templated 3' bases by reverse transcriptase during first-strand cDNA synthesis. It cannot be excluded that the 5' terminus of HCV genome RNA contains a 5' cap structure or a covalently-linked terminal protein such as VPg of the picornaviruses. For the pestiviruses, recent studies suggest that genome RNAs may not contain a 5' cap (Brock et al (1992) *J. Virol. Meth.* 38:39–46) and that this structure is not required for infectivity of transcribed RNA (R. Donis, R. J. Moorman, personal communications). Consistent with these observations, neither HCV nor the pestiviruses contain motifs characteristic of virus-encoded enzymes involved in capping or methylation of cap structures (Rice (1995)). There is the possibility of a protein covalently-linked to the 5' terminus of HCV genome RNA, but synthetic RNA transcripts corresponding to viruses that normally contain such 5' structures are infectious, indicating that they are usually not an absolute requirement for initiation of replication.

EXAMPLE 1

Structure of the HCV-H 3' NTR. Determination of the extreme 3' terminal HCV sequences presented a greater challenge. Due to limited quantities of HCV genome RNA, the classic method of 3'-end labeling and direct RNA sequence analysis has not been feasible. One of the first reports suggested that HCV RNAs contained 3' terminal poly (A) tracts (for HCV-1) Han et al (1991) used tagged oligo (dT) primers for cDNA synthesis followed by PCR amplification, cloning and sequence analysis. This is not an acceptable method for 3' end determination as it already presupposes a 3' poly (A) or polypurine tract and would select for such RNAs even if they were present in low abundance. Some reports utilized *E. coli* poly (A) polymerase to add 3' homopolymer tracts prior to oligo (dT)-primed cDNA synthesis and found evidence of a 3' terminal poly (U) (i.e., Kato et al, 1990) or isolated 3' clones with poly (U) tracts from randomly primed cDNA libraries. To actually determine the 3' terminal sequence and to solve this contradiction [3' poly (A) versus poly (U)], 5' RACE was used to determine the 5' terminal sequence of HCV negative-strand RNA (Chen et al, 1992). This study predicted a 3' terminal poly (U) tract for the HCV genome RNA. Subsequently, other groups have not attempted to determine actual 3' termini, but rather assumed a 3' poly (U) tract and used oligo (dA) for priming cDNA synthesis or isolated 3' clones with poly (U) tracts from randomly primed cDNA libraries. Depending upon the actual 3' structure, all of these approaches have potential problems (some are discussed below) and a critical reading of the literature makes it clear that the 3' end of the genome RNA has until now been poorly characterized and uncertain at best. Alternative approaches for determining the terminal sequence of HCV-H were therefore pursued.

One such approach, mentioned above for 5' end determination, is to cyclize the RNA using T4 RNA ligase followed by cDNA synthesis and amplification using a negative-sense primer complementary to a sequence in the 5' NTR and a positive-sense primer near the 3' end (Mandl et al, 1991). Ideally, cloning and sequence analysis of such products should provide information on 5' and 3' terminal sequences present in the same RNA molecule. In the case of HCV, since the 5' terminus has been reasonably well-defined by other methods, these data should allow determination of the 3' terminus. Unfortunately, despite repeated attempts, this method has failed for determination of HCV-H terminal sequences (even using RNA obtained from high specific-infectivity plasma). Potential problems include (i) a blocked 5' terminus (ii) lack of a 3' —OH group or a poor acceptor for RNA ligase (such as a U residue; Moore and Sharp, 1992) (iii) ribonuclease activity during RNA preparation or RNA ligation (see below) or (iv) terminal RNA structures sterically inhibiting 5'–3' ligation. In any case, recent work has shown this method to be unreliable, even when using large quantities of purified, initially intact TBE genome RNA. Likely problems include Rakes contamination in most commercial preparations of tobacco acid pyrophosphatase and T4 RNA ligase (A. A. Kolykhalov, unpublished data) and probable hypersensitivity of the poly (U)/polypyrimidine tract to the action of RNases. In any case, poly (A) was incorrectly assigned as the terminal sequence of TBE genome RNA, whereas later experiments demonstrated that such poly (A) tracts were internal and followed by additional sequences including a 3' terminal hairpin structure (C. Mandl, personal communication). Interestingly, the correct 3' structure, but not the poly (A) tract, is required for infectivity of transcribed TBE RNA (C. Mandl, personal communication).

Figure 1:
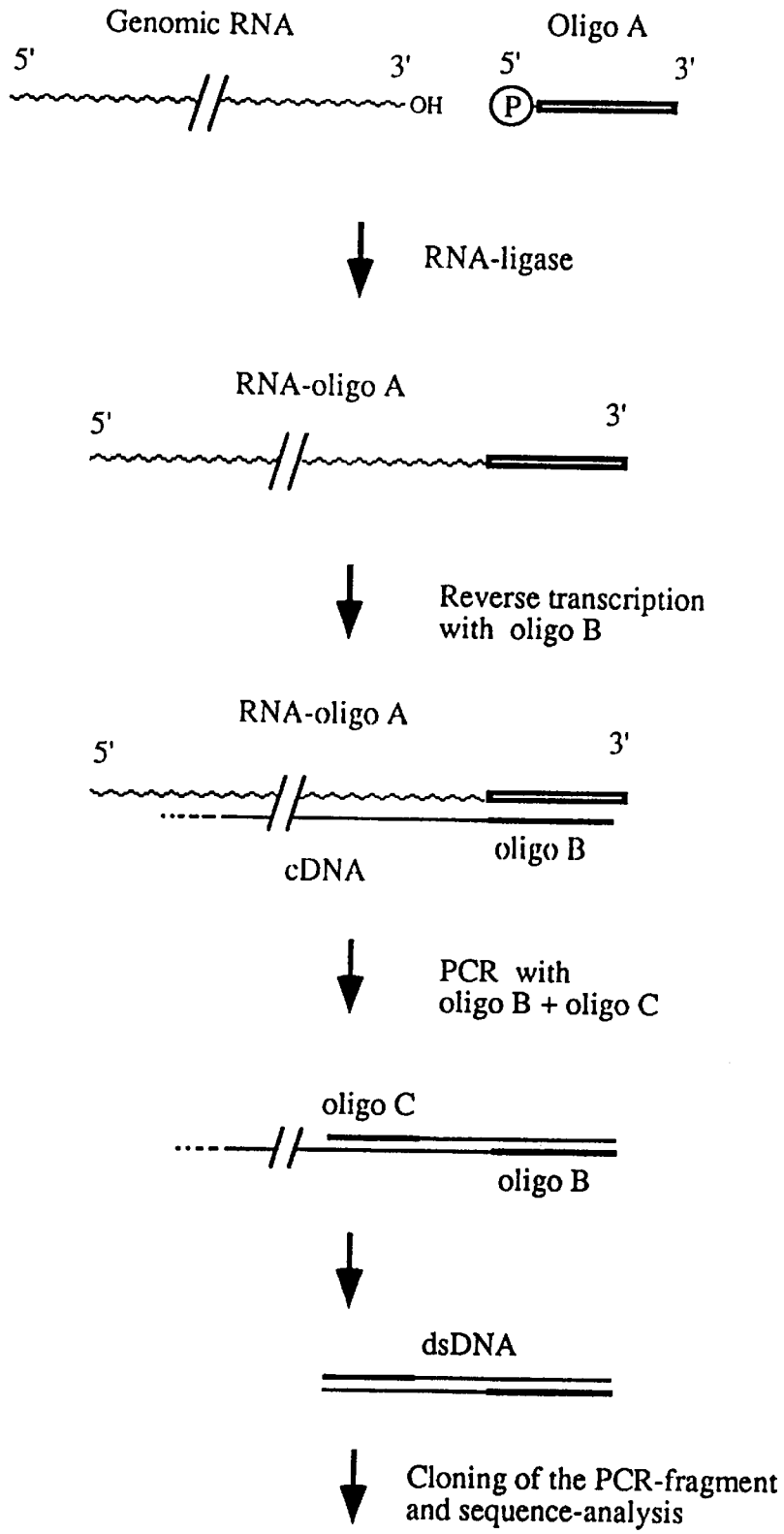

Two other methods were considered. For determining the YF 3' terminus, *E. coli* poly (A) polymerase had been used to add 3' terminal poly (A), followed by oligo (dT) priming and a selective cloning strategy. The YF 3' terminus was cloned with great difficulty and found to be a highly stable hairpin structure (Hahn et al, 1987; Rice et al, 1985). However, this approach was not considered since addition of 3' poly (A) would allow self-priming at the HCV poly (U) tract and subsequent elimination of potential sequences in between during second-strand cDNA synthesis and cloning. Rather, an alternative 3' RACE method was used in which a synthetic oligodeoxynucleotide, present at high concentrations, was ligated to the 3' end of the RNA to serve as a specific priming site for cDNA synthesis (FIG. 1). Ligation conditions were optimized by assaying the ability of T4 RNA ligase to ligate 5'-end-labeled oligonucleotides to a synthetic acceptor RNA (Brennan et al (1983) *Meth. Enz.* 100:38–52). Critical parameters included the batch of RNA ligase (many were heavily contaminated with RNase), the concentration of DMSO (20–30%), and the particular oligonucleotide used for ligation (A. A. Kolykhalov, unpublished). For the 3' analysis of HCV-H, $10^4$ molecules of RNA were purified from high-titered H77 plasma, ligated to the synthetic oligonucleotide, and this modified RNA used for RT/PCR (FIG. 1). One primer for cDNA synthesis and PCR amplification (oligo B—SEQ ID NOS:6 and 7) was complementary to that used for ligation to the RNA (oligo A—SEQ ID NO:5); a second positive-sense primer corresponded to a sequence near the 3' end of the HCV ORF (oligo C—SEQ ID NO:8).

Figure 4:
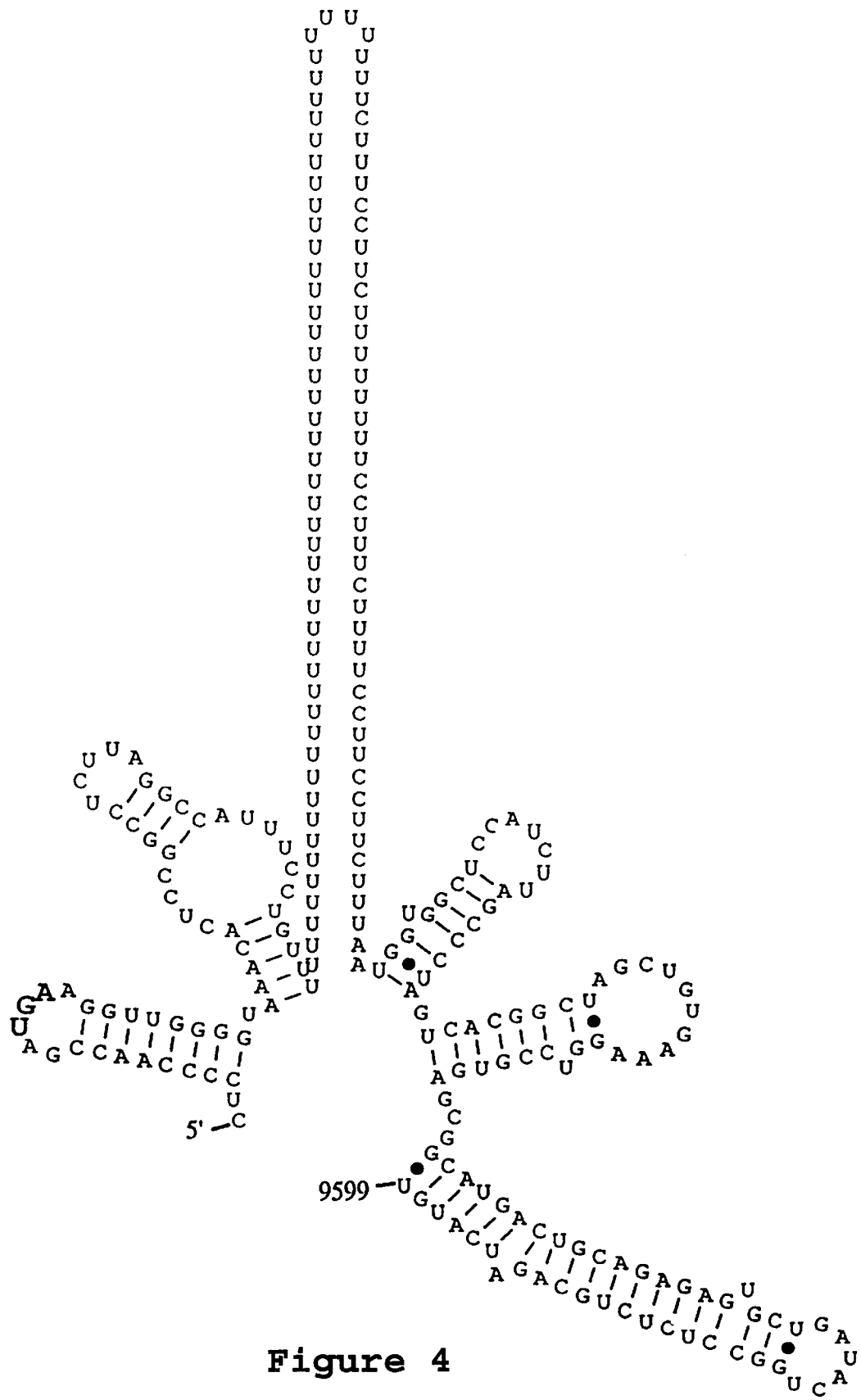
FIG. 4 depicts the computer predicted (FOLDRNA, GCG package) secondary structure of the 3' end of HCV-H (SEQ ID NO:25). The last 46 nucleotides form a stable stem-loop structure (predicted energy −25 kCal/mol).

A smear of amplified products, as resolved by agarose gel electrophoresis, was obtained after 40 cycles of PCR amplification. This DNA was either subjected to additional PCR analyses or cloned directly for sequence determinations. The presence of predicted internal HCV sequences and homopolymer tracts was assayed using a nested positive sense primer and either oligo (dA) or oligo (dT). A product of the expected size (based on previous HCV 3' NTR sequences) was obtained using the oligo (dA) primer; no product was found using oligo (dT). Prototype HCV cDNA clones terminating in either poly (A) or poly (T) served as positive and negative controls for these primer pairs and gave the expected results. These data strongly suggest that HCV-H does not contain poly (A) but rather, as found for most HCV isolates, contains a poly (U) tract [or at least a site for priming by oligo (dA)] at or near its 3' terminus. From the cloned material [which had not be subjected to further amplification using oligo (dA)], sequences from 20 independent clones were determined. Essentially all of these clones contained (5' to 3', positive-sense) (i) the previously determined HCV-H sequence (Inchauspe et al (1991) *Proc. Nati. Acad. Sci. USA* 88:10292–10296) (ii) 40 bases homologous to other HCV isolates (FIG. 2) (iii) poly (U) tracts of various lengths and (iv) the sequence of the oligonucleotide used for RNA ligation. Five independent clones, derived from two different PCR amplification experiments, were found to have unusual structures. Following variable lengths of poly (U) and polypyrimidine stretches consisting of mainly U with occasional interspersed C residues, four of these clones contained a novel sequence of 101 bases (SEQ ID NO:1) which was nearly identical in all clones (two clones differed by 1 substitution each; 1 clone terminated after only 39 bases of this sequence) (FIG. 3). This 101 base sequence, particularly the 3' terminal 46 bases, is predicted (FOLDRNA, GCG package) to form a highly stable secondary structure reminiscent of the 3' termini of members of the flavivirus genus (Chambers et al (1990) *Virology* 177:159–174) (FIG. 4). However, an exhaustive search (BLAST, FASTA) of the databases has revealed no entry showing significant homology to this novel HCV sequence.

Several lines of evidence suggest that this 101 base sequence is not an RT/PCR artifact and represents the 3' terminal sequence of HCV genome RNA.

First, as mentioned above, HCV-H clones with similar but not identical structures were obtained from two independent experiments (FIG. 3). These clones differed in the length of the poly (U)/polypyrimidine tract and by a few base substitutions within the 101 base element, but the sequences across the breakpoint between the novel sequence and the ligated oligonucleotide were identical in four clones.

In a second set of experiments, negative-sense oligonucleotides were designed based on the sequence of the 101-base element, and used for RT/PCR amplification and cloning of HCV RNA from either HCV-H or four different clinical samples obtained from investigators around the country. Samples were obtained from patients with chronic hepatitis C and all were HCV RNA positive and of different genotypes (1b, 3 and two samples of genotype 4) than previously analyzed HCV-H(1a). Multiple independent clones were obtained and sequenced (FIG. 6) for each amplified sample. As described above, for HCV-H, all clones contained identical sequences at the end of the ORF and the 3' NTR sequence preceding the poly (U)/polypyrimidine tract. This poly (U)/polypyrimidine tract was variable in length and followed by the novel 3' element. Clones from the other isolates had similar structures except that genotype-specific differences were observed in the ORF and 3' NTR sequence preceding the poly (U)/polypyrimidine tract. The sequence of the novel 3' element was present and absolutely identical in all of these clones suggesting that this element is both present in the genome RNAs of distinct genotypes and highly conserved. This experiment also proves that this structure is not an in vitro artifact generated by T4 RNA ligase.

This analysis demonstrated that the novel 3' element was present in other HCV genotypes, but did not define the actual 3' end of these genome RNAs. Using a similar RNA ligation procedure (FIG. 7), the 3' terminal sequences of these different HCV genotypes were determined. The same novel 3' terminal sequence (with one or two isolate-specific substitutions) was found joined, at exactly the same breakpoint, to the sequence of the oligonucleotide used for T4 RNA ligation (FIG. 8).

A fourth experiment provides yet more evidence that the 3' novel sequence represents the 3' terminus of HCV genome RNA. It could be argued that clones with the novel structure could be obtained by internal priming within the 3' NTR if, by chance, the 3' portion of the synthetic primer used for cDNA synthesis (and PCR amplification) was complementary to a sequence within the HCV 3' NTR. To address this concern, the analysis was repeated using serum from a different patient (WD) and a distinct oligonucleotide ("oligo G"; SEQ ID NO:37) in the RNA ligation step, whose sequence was not homologous to the oligonucleotide used in the initial experiments. The complement of this oligonucleotide ("oligo H"; SEQ ID NO:38)was used for cDNA synthesis and PCR amplification together with "oligo F" (SEQ ID NO:32), and the products were cloned and sequenced. The same novel 3' terminal sequence was found joined, at exactly the same breakpoint, to the sequence of the alternative synthetic oligonucleotide.

This novel 3' NTR structure appears to be highly conserved among HCV isolates and is likely to be an essential RNA element required for virus replication and successful recovery of infectious HCV RNA from cDNA.

Based on these data, the current picture of HCV-H genome structure is diagrammed in FIG. 10. The genome RNA probably initiates with a G residue and contains a 5' NTR of 341 bases. The ORF consists of 9033 bases encoding a polyprotein of 3011 amino acid residues. Following the opal (UGA) stop codon is a sequence of 40 bases, a poly (U) tract, a polypyrimidine stretch, and a highly conserved RNA element of about 100 bases. Some positive-strand RNA viruses (poliovirus, Sindbis virus) contain 3' terminal poly (A) but many others terminate with conserved RNA sequences which can often be folded into stable secondary structures (bromoviruses, flaviviruses). Besides TBE isolates containing internal poly (A) followed by a 3' terminal secondary structure, there is one other example of a virus which contains a 3' NTR similar to that proposed here for HCV. This virus, called GBV-B, is one of the newly cloned and sequenced GB hepatitis agents (Simons et al (1995) *Proc. Natl. Acad. Sci. USA* 92:3401–5). These two isolates (GBV-A and GBV-B) together with HGV (an agent cloned by Genelabs) appear to be most closely related to HCV. All appear to have positive-strand genome RNAs of ~9–10 kb and a single long ORF encoding proteins with significant homology to those of HCV. In the case of GBV-B, the 3'

NTR consists of 27 bases, a poly (U) tract, and an additional sequence of 49 bases (Simons et al, 1995). Other than the poly (U) tract, this sequence shows no significant homology with the HCV-H 3' NTR (A. A. Kolykhalov, unpublished).

Discussion

The present invention provides sequence data which demonstrate that the genome RNA of HCV-H (a type 1a isolate) appears not to terminate with a homopolymer tract as previously thought, but rather with a novel sequence of 101 bases. Furthermore, results suggest that this 3' NTR structure and the putative 3' terminal element may be features common to other HCV genotypes. In addition to the potential importance of the 3' NTR for HCV replication and recovery of authentic HCV from cDNA, the apparent conservation of the conserved 3' element has important applications for HCV diagnostics and therapy. Determination of HCV RNA levels in patient plasma and tissues is important not only for diagnosis of HCV infection in the absence of antibody response but also for following the efficacy of therapeutic regimens (Bresters et al (1994) *J. Med. Virol.* 43:262–8; Cha et al (1991) *J. Clin. Microbiol.* 29:2528–34; Chazouilleres et al (1994) *Gastroenterology* 106:994–9; Davis et al (1994) *Hepatology* 19:1337–41; Feray et al (1994) *Hepatology* 20:1137–43; Gordon et al (1994) *Am. J. Gastroenterol.* 89:1458–61; Simmonds et al (1994) *J. Gen. Virol.* 75:1053–1061; Wright et al (1994) *Hepatology* 20:773–9). Current methods, such as quantitative RT/PCR or branched DNA, rely on conserved RNA targets in the HCV genome which can be either genus-, type-, or subtype-specific. Detection of this novel, conserved sequence may be a useful alternative for diagnosis of HCV infection. In terms of therapy, highly conserved elements in RNA virus genomes have, in most cases, been shown to be essential for efficient virus replication. Such elements, via interaction with viral and/or host factors, function in translation of the incoming viral RNA, as promoters for negative- and positive-strand RNA synthesis, and as signals for selective packaging of viral RNAs. A conserved 3' element in the HCV genome, which is likely to be important for one or more of these processes, presents an attractive therapeutic target. Identification of compounds which block interaction of this element with its cognate host or viral factors or gene therapy approaches using this element as an RNA decoy (Sullenger et al (1990) *Cell* 63:601–608) in transplanted hepatocytes may prove useful in eradicating or controlling chronic HCV infections.

The present invention demonstrates that there may be an association of the novel sequence element and HCV infection. The novel 3' sequence element may be used for (i) constructing full-length HCV-H cDNA clones capable of yielding infectious RNA and virus (vaccine development, evaluation of therapeutic compounds); (ii) engineering functional HCV RNA replicons for HCV replication studies and therapeutic evaluation; (iii) the determination of 3' NTR sequences for other HCV genotypes and a phylogenetic analysis to define areas of conservation and divergence (nucleic acid based diagnostics for HCV detection); (iv) the improvement of methods for determining the HCV 3' NTR sequences and an examination of possible correlations between HCV 3' NTR features and clinical parameters (disease severity, IFN response, immune status) or tissue tropism (predictive diagnostics); (v) determination of the 3' NTR secondary structure using chemical modification and RNase mapping and determination of 3D structure by NMR; (vi) structure/function studies on the 3' NTR using the infectious clone (therapy, vaccine development); (vii) definition of host or viral factors which interact with the sequence (therapy); (viii) setting up screening assays to identify compounds which inhibit the interaction of the element with its cognate host and/or viral factors and to test identified compounds for their effects on HCV replication (therapy); (ix) testing the conserved 3' NTR sequence element as a trans-dominant inhibitor of HCV replication (gene therapy).

The following is a list of documents related to the above disclosure and particularly to the experimental procedures and discussions. The documents are numbered to correspond to like number documents that may appear hereinabove.

1. Alter, H. J.; Purcell, R. H.; Holland, P. V.; and Popper, H. (1978). Transmissible agent in non-A, non-B hepatitis. *Lancet* 1:459–463.
2. Alter, M. J.; Hadler, S. C.; Judson, F. N.; Mares, A.; Alexander, W. J.; Hu, P. Y.; Miller, J. K.; Moyer, L. A.; Fields, H. A.; Bradley, D. W.; and Margolis, H. S. (1990). Risk factors for acute noni-A, non-B hepatitis in the United States and association with hepatitis C virus infection. *J. Am. Med. Assoc.* 264:2231–2235.
3. Alter, M. J.; Margolis, H. S.; Krawczynski, K.; Judson, F. N.; Mares, A.; Alexander, W. J.; Hu, P. Y.; Miller, J. K.; Gerber, M. A.; Sampliner, R. E.; Meeks, E. L.; and Beach, M. J. (1992). The natural history of community-acquired hepatitis C in the United States. *N. Eng. J. Med.* 327:1899–1905.
4. Bertolini, L.; Iacovacci, S.; Ponzetto, A.; Gorini, G.; Battaglia, M.; and Carloni, G. (1993). The human bone-marrow-derived B-cell line CE, susceptible to hepatitis C virus infection. *Res. Virol.* 144:281–285.
5. Blight, K.; Rowland, R.; Hall, P. D.; Lesniewski, R. R.; Trowbridge, R.; LaBrooy, J. T.; and Gowans, E. J. (1993). Immunohistochemical detection of the NS4 antigen of hepatitis C virus and its relation to histopathology. *Amer. J. Path.* 143: 1568–1573.
6. Blight, K.; Trowbridge, R.; Rowland, R.; and Gowans, E. (1992). Detection of hepatitis C virus RNA by in situ hybridization. *Liver* 12:286–289.
7. Bouffard, P.; Hayashi, P. H.; Acevedo, R.; Levy, N.; and Zeldis, J. B. (1992). Hepatitis C virus is detected in a monocyte/macrophage subpopulation of peripheral blood mononuclear cells of infected patients. *J. Inf. Dis.* 166:1276–1280.
8. Boyer, J.-C., and Haenni, A.-L. (1994). Infectious transcripts and cDNA clones of RNA viruses. *J. Gen. Virol.* 198: 415–426.
9. Bradley, D.; McCaustland, K.; Krawczynski, K.; Spelbring, J.; Humphrey, C.; and Cook, E. H. (1991). Hepatitis C virus: Buoyant density of the factor VIII-derived isolate in sucrose. *J. Med. Virol.* 34:206–208.
10. Bradley, D. W. (1990). Hepatitis non-A, non-B viruses become identified as hepatitis C and E viruses. *Prog. Med. Virol.* 37:101–135.
11. Bradley, D. W.; Maynard, J. E.; Popper, H.; Cook, E. H.; Ebert, J. W.; McCaustland, K. A.; Schable, C. A.; and Fields, H. A. (1983). Posttransfusion non-A, non-B hepatitis: Physicochemical properties of two distinct agents. *J. Infect. Dis.* 148:254–265.
12. Bradley, D. W.; McCaustland, K. A.; Cook, E. H.; Schable, C. A.; Ebert, J. W.; and Maynard, J. E. (1985). Posttransfusion non-A, non-B hepatitis in Chimpanzees: Physicochemical evidence that the tubule-forming agent is a small, enveloped virus. *Gastroenterology* 88:773–779.
13. Brennan, C. A.; Manthey, A. E.; and Gumport, R. I. (1983). Using T4 RNA ligase with DNA substrates. *Meth. Enz.* 100:38–52.

14. Bresters, D.; Cuypers, H. T.; Reesink, H. W.; Mauser-Bunschoteln, E. P.; van den Berg, H. M.; Schaasberg, W. P.; Wilber, J. C.; Urdea, M. S.; Neuwald, P.; and Lelie, P. N. (1994). Comparison of quantitative cDNA-PCR with the branched DNA hybridization assay for monitoring plasma hepatitis C virus RNA levels in hemophilia patients participating in a controlled interferon trial. *J. Med. Virol.* 43:262–8.

15. Brock, K. V.; Deng, R.; and Riblet, S. M. (1992). Nucleotide sequencing of 5' and 3' termini of bovine viral diarrhea virus by RNA ligation and PCR. *J. Virol. Meth.* 38:39–46.

16. Brown, E. A.; Zhang, H.; Ping, L. H.; and Lemon, S. M. (1992). Secondary structure of the 5' nontranslated regions of hepatitis C virus and pestivirus genomic RNAs. *Nucl. Acids Res.* 20:5041–5045.

17. Bukh, J.; Miller, R. H.; and Purcell, R. H. (1995). Genetic heterogeneity of hepatitis C virus: Quasispecies and genotypes. *Sem. Liver Dis.* 15:41–63.

18. Bukh, J.; Purcell, R. H.; and Miller, R. H. (1992). Sequence analysis of the 5' noncoding region of hepatitis C virus. *Proc. Natl. Acad. Sci. USA* 89:4942–4946.

19. Carloni, G.; Iacovacci, S.; Sargiacomo, M.; Ravagnan, G.; Ponzetto, A., Peschle, C.; and Battaglia, M. (1993). Susceptibility of human liver cell cultures to hepatitis C virus infection. *Arch. Virol.* Suppl. 8:31–39.

20. Carrick, R. J.; Schlauder, G. G.; Peterson, D. A.; and Mushahwar, I. K. (1992). Examination of the buoyant density of hepatitis C virus by the polymerase chain reaction. *J. Virol. Meth.* 39:279–289.

21. Cha, T. A.; Kolberg, J.; Irvine, B.; Stempien, M.; Beall, E.; Yano, M.; Choo, Q. L.; Houghton, M.; Kuo, G.; Han, J. H.; and Urdea, M. S. (1991). Use of a signature nucleotide sequence of the hepatitis C virus for the detection of viral RNA in human serum and plasma. *J. Clin. Microbiol.* 29:2528–34.

22. Chambers, T. J.; McCourt, D. W.; and Rice, C. M. (1990). Production of yellow fever virus proteins in infected cells: Identification of discrete polyprotein species and analysis of cleavage kinetics using region-specific polyclonal antisera. *Virology* 177:159–174.

23. Chazouilleres, O.; Kim, M.; Combs, C.; Ferrell, L.; Bacchetti, P.; Roberts, J.; Ascher, N. L.; Neuwald, P.; Wilber, J.; Urdea, M.; and et al. (1994). Quantitation of hepatitis C virus RNA in liver transplant recipients. *Gastroenterology* 106:994–9.

24. Chen, P.-J.; Lin, M.-H.; Tai, K.-F.; Liu, P.-C.; Lin, C.-J.; and Chen, D.-S. (1992). The Taiwanese hepatitis C virus genome: Sequence determination and mapping the 5' termini of viral genomic and antigenomic RNA. *Virology* 188:102–113.

25. Choo, Q.-L.; Kuo, G.; Ralston, R.; Weiner, A.; Chien, D.; Van Nest, G.; Han, J.; Berger, K.; Thudium, K.; Kuo, C.; Kansopon, J.; McFarland, J.; Tabrizi, A.; Ching, K.; Moss, B.; Cummins, L. B.; Houghton, M.; and Muchmore, E. (1994). Vaccination of chimpanzees against infection by the hepatitis C virus. *Proc. Natl. Acad. Sci. USA* 91:1294–1298.

26. Choo, Q.-L.; Kuo, G.; Weiner, A. J.; Overby, L. R.; Bradley, D. W.; and Houghton, M. (1989). Isolation of a cDNA clone derived from a blood-borne non-A, non-B viral hepatitis genome. *Science* 244:359–362.

27. Davis, G. L.; Balart, L. A.; Schiff, E. R.; Lindsay, K.; Bodenheimer Jr., H. C.; Perrillo, R. P.; Carey, W.; Jacobson, 1. M.; Payne, J.; Dienstag, J. L.; VanThiel, D. H.; Tamburro, C.; Lefkowitch, J.; Albrecht, J.; Maschievitz, C.; Ortego, T. J.; and Gibas, A. (1989). Treatment of chronic hepatitis C with recombinant interferon alpha: A multicenter randomized, controlled trial. *N. Engl. J. Med.* 321:1501–1506.

28. Davis, G. L.; Lau, J. Y.; Urdea, M. S.; Neuwald, P. D.; Wilber, J. C.; Lindsay, K.; Perrillo, R. P.; and Albrecht, J. (1994). Quantitative detection of hepatitis C virus RNA with a solid-phase signal amplification method: definition of optimal conditions for specimen collection and clinical application in interferon-treated patients. *Hepatology* 19:1337–41.

29. DiBisceglie, A. M.; Martin, P.; Kassianides, C.; Lisker-Melman, M.; Murray, L.; Waggoner, J. G.; Goodman, Z.; Banks, S. M.; and Hoofnagle, J. H. (1989). Recombinant interferon alpha therapy for chronic hepatitis C: A randomized, double-blind, placebo-controlled trial. *New Engl. J. Med.* 321:1506–1510.

30. Dubuisson, J.; Hsu, H. H.; Cheung, R. C.; Greenberg, H.; Russell, D. R.; and Rice, C. M. (1994). Formation and intracellular localization of hepatitis C virus envelope glycoprotein complexes expressed by recombinant vaccinia and Sindbis viruses. *J. Virol.* 68:6147–6160.

31. Enomoto, N.; Sakamoto, N.; Kurosaki, M.; Marumo, F.; and Sato, C. (1993). The hypervariable region of the HCV genome changes sequentially during the progression of acute HCV infection to chronic hepatitis. *J. Hepatol.* 17:415–416.

32. Farci, P.; Alter, H. J.; Govindarajani, S.; Wong, D. C.; Engle, R.; Lesniewski, R. R.; Mushahwar, I. K.; Desai, S. M.; Miller, R. H.; Ogata N.; and Purcell, R. H. (1992). Lack of protective immunity against reinfection with hepatitis C virus. *Science* 258:135–140.

33. Feinstone, S. M.; Mihalik, K. B.; Kamimura, T.; Alter, H. J.; London, W. T.; and Purcell, R. H. (1983). Inactivation of hepatitis B virus and non-A, non-B hepatitis by chloroform. *Infect. Immun.* 41:816–821.

34. Feray, C.; Gigou, M.; Samuel, D.; Paradis, V.; Wilber, J.; David, M. F.; Urdea, M.; Reynes, M.; Brechot, C.; and Bismuth, H. (1994). The course of hepatitis C virus infection after liver transplantation. *Hepatology* 20:1137–43.

35. Ferri, C.; La Civita, L.; Longombardo, G.; Greco, F.; and Bombardieri, S. (1993). Hepatitis C virus and mixed cryoglobulinemia. *Eur. J. Clin. Invest.* 23:399–405.

36. Fong, T. L.; Shindo, M.; Feinstonie, S. M.; Hoofnagle, J. H.; and Di Bisceglie, A. M. (1991). Detection of replicative intermediates of hepatitis C viral RNA in liver and serum of patients with chronic hepatitis C. *J. Clin. Invest.* 88:1058–1060.

37. Francki, R. I. B.; Fauquet, C. M.; Knudson, D. L.; and Brown, F. (1991). Classification and nomenclature of viruses: Fifth report of the international committee on taxonomy of viruses. *Arch. Virol. Suppl.* 2:223.

38. Fukushi, S.; Katayama, K.; Kurihara, C.; Ishiyama, N.; Hoshino, F. B.; Ando, T.; and Oya, A. (1994). Complete 5' noncoding region is necessary for the efficient internal initiation of hepatitis C virus RNA. *Biochem. Biophys. Res. Comm.* 199:425–432.

39. Gil, B.; Qian, C.; Riezu-Boj, J. I.; Civeira, M. P.; and Prieto, J. (1993). Hepatic and extrahepatic HCV RNA strands in chronic hepatitis C: different patterns of response to interferon treatment. *Hepatology* 18:1050–1054.

40. Gordon, S. C.; Kodali, V. P.; Silverman, A. L.; Dmuchowski, C. F.; Urdea, M. S.; Chan, C. S.; and Wilber, J. C. (1994). Levels of hepatitis C virus RNA and liver histology in chronic type C hepatitis. *Am. J. Gastroenterol.* 89:1458–61.

41. Greiser-Wilke, I.; Dittmar, K. E.; Liess, B.; and Moennig, V. (1991). Immunofluorescence studies of biotype-specific expression of bovine viral diarrhoea virus epitopes in infected cells. *J. Gen. Virol.* 72:2015–2019.
42. Gunji, T.; Kato, N.; Hijikata, M.; Hayashi, K.; Saitoh, S.; and Shimotohno, K. (1994). Specific detection of positive and negative stranded hepatitis C viral RNA using chemical RNA modification. *Arch. Virol.* 134:293–302.
43. Hahn, C. S.; Hahn, Y. S.; Rice, C. M.; Lee, E.; Dalgarno, L.; Strauss, E. G.; and Strauss, J. H. (1987). Conserved elements in the 3' untranslated region of flavivirus RNAs and potential cyclization sequences. *J. Mol. Biol.* 198:33–41.
44. Han, J. H.; Shyamala, V.; Richman, K. H.; Brauer, M. J.; Irvine, B.; Urdea, M. S.; Tekamp-Olson, P.; Kuo, G.; Choo, Q.-L.; and Houghton, M. (1991). Characterization of the terminal regions of hepatitis C viral RNA: Identification of conserved sequences in the 5' untranslated region and poly(A) tails at the 3' end. *Proc. Natl. Acad. Sci. USA* 88:1711–1715.
45. Haruna, Y.; Hayashi, N.; Hiramatsu, N.; Takehara, T.; Hagiwara, H.; Sasaki, Y.; Kasahara, A.; Fusamoto, H.; and Kamada, T. (1993). Detection of hepatitis c virus RNA in liver tissues by an in situ hybridization technique. *J. Hepatol.* 18:96–100.
46. He, L. F.; Alling, D.; Popkin, T.; Shapiro, M.; Alter, H. J.; and Purcell, R. H. (1987). Determining the size of non-A, non-B hepatitis by filtration. *J. Infect. Dis.* 156:636–640.
47. Hibbs, R. G.; Corwin, A. L.; Hassan, N. F.; Kamel, M.; Darwislh, M.; Edelman, R.; Constantine, N. T.; Rao, M. R.; Khalifa, A. S., and Mokhtar, S. (1993). The epidemiology of antibody to hepatitis C in Egypt. *J. Inf. Dis.* 168:789–790.
48. Higashi, Y.; Kakumu, S.; Yoshioka, K.; Wakita, T.; Mizokami, M.; Ohba, K.; Ito, Y.; Ishikawa, T.; Takayanagi, M.; and Nagai, Y. (1993). Dynamics of genome change in the E2/NS1 region of hepatitis C virus in vivo. *Virology* 197:659–668.
49. Hijikata, M.; Kato, N.; Ootsuyama, Y.; Nakagawa, M.; Ohkoshi, S.; and Shimotohno, K. (1991). Hypervariable regions in the putative glycoprotein of hepatitis C virus. *Biochem. Biophys. Res. Comm.* 175:220–228.
50. Hijikata, M.; Shimizu, Y. K.; Kato, H.; Iwamoto, A.; Shih, J. W.; Alter, H. J.; Purcell, R. H.; and Yoshikura, H. (1993). Equilibrium centrifugation studies of hepatitis C virus: Evidence for circulating immune complexes. *J. Virol.* 67:1953–1958.
51. Hiramatsu, N.; Hayashi, N.; Haruna, Y.; Kasahara, A.; Fusamoto, H.; Mori, C.; Fuke, I.; Okayama, H.; and Kamada, T. (1992). Immunohistochemical detection of hepatitis C virus-infected hepatocytes in chronic liver disease with monoclonal antibodies to core, envelope and NS3 regions of the hepatitis C virus genome. *Hepatology* 16:306–311.
52. Hollinger, F. B.; Gitnick, G.; Aach, R. D.; Szmuness, W., Mosley; J. W.; Stevens, C. E.; Peters, R. L.; Weiner, J. M.; Werch, J. B.; and Lander, J. J. (1978). Non-A, non-B hepatitis transmission in chimpanzees: A project of the transfusion-transmitted viruses study group. *Intervirology* 10: 60–68.
53. Houghton, M.; Selby, M.; Weiner, A.; and Choo, Q. L. (1994). Hepatitis C virus: Structure, protein products and processing of the polyprotein precursor. [Review]. *Curr. Stud. Hematol. Blood Transfus.* 61:1–11.
54. Iacovacci, S.; Sargiacomo, M.; Parolini, I.; Ponzetto, A.; Peschle, C.; and Carloni, G. (1993). Replication and multiplication of hepatitis C virus genome in human foetal liver cells. *Res. Virol.* 144:275–279.
55. Inchauspe, G.; Zebedee, S.; Lee, D.-H.; Sugitani, M.; Nasoff, M.; and Prince, A. M. (1991). Genomic structure of the human prototype strain H of hepatitis C virus: Comparison with American and Japanese isolates. *Proc. Natl. Acad. Sci. USA* 88:10292–10296.
56. Kagawa, T.; Saito, H.; Tada, S.; Tsunematsu, S.; Morizane, T.; and Tsuchiya, M. (1993). Is hepatitis C virus cytopathic? *Lancet* 341:316–317.
57. Kanto, T.; Hayashi, N.; Takehara, T.; Hagiwara, H.; Mita, E.; Naito, M.; Kasahara, A.; Fusamoto, H.; and Kamada, T. (1994). Buoyant density of hepatitis C virus recovered from infected hosts: Two different features in sucrose equilibrium density-gradient centrifugation related to degree of liver inflammation. *Hepatology* 19:296–302.
58. Kato, N.; Nakazawa, T.; Mizutani, T.; and Shimotohno, K. (1995). Susceptibility of human T-lymphotropic virus type I infected cell line MT-2 to hepatitis C virus infection. *Biochem. Biophys. Res. Commun.* 206:863–9.
59. Kato, N.; Ootsuyama, Y.; Ohkoshi, S.; Nakazawa, T.; Sekiya, H.; Hijikata, M.; and Shimotohno, K. (1992). Characterization of hypervariable regions in the putative envelope protein of hepatitis C virus. *Biochem. Biophys. Res. Comm.* 189:119–127.
60. Kato, N.; Sekiya, H.; Ootsuyama, Y.; Nakazawa, T.; Hijikata, M.; Ohkoshi, S.; and Shimotohno, K. (1993). Humoral immune response to hypervariable region 1 of the putative envelope glycoprotein (gp70) of hepatitis C virus. *J. Virol.* 67:3923–3930.
61. Kato, N.; Hijikata, M.; Ootsuyama, Y.; Nakagawa, M.; Ohkoshi, S.; Sugimura, T.; and Shimotohno, K. (1990). Molecular cloning of the human hepatitis C virus genome from Japanese patients with non-A, non-B hepatitis. *Proc. Natl. Acad. Sci. USA* 87:9524–9528.
62. Kolykhalov, A. A.; and Rice, C. M. (1996). In preparation.
63. Krawczynski, K.; Beach, M. J.; Bradley, D. W.; Kuo, G.; di Bisceglie, A. M.; Houghton, M.; Reyes, G. R.; Kim, J. P.; Choo, Q. L.; and Alter, M. J. (1992). Hepatitis C virus antigen in hepatocytes: immunomorphologic detection and identification. *Gastroenterology* 103:622–629.
64. Kurosaki, M.; Enomoto, N.; Marumo, F.; and Sato, C. (1993). Rapid sequence variation of the hypervariable region of hepatitis C virus during the course of chronic infection. *Hepatology* 18:1293–1299.
65. Lamas, E.; Baccarini, P.; Housset, C.; Kremsdorf, D.; and Brechot, C. (1992). Detection of hepatitis C virus (HCV) RNA sequences in liver tissue by in situ hybridization. *J. Hepatol.* 16:219–223.
66. Lanford, R. E.; Sureau, C.; Jacob, J. R.; White, R.; and Fuerst, T. R. (1994). Demonstration of in vitro infection of chimpanzee hepatocytes with hepatitis C virus using strand-specific RT/PCR. *Virology* 202:606–614.
67. Lesniewski, R. R.; Boardway, K. M.; Casey, J. M.; Desai, S. M.; Devare, S. G.; Leung, T. K.; and Mushalhwar, I. K. (1993). Hypervariable 5'-terminus of hepatitis C virus E2/NS1 encodes antigenically distinct variants. *J. Med. Virol.* 40:150–156.
68. Lin, C.; Lindenbach, B. D.; Pragai, B.; McCourt, D. W.; and Rice, C. M. (1994). Processing of the hepatitis C virus E2-NS2 region: Identification of p7 and two distinct E2-specific products with different C termini. *J. Virol.* 68:5063–5073.
69. Mandl, C. W.; Heinz, F. X.; Puchhammer-Stockl, E.; and Kunz, C. (1991). Sequencing the termini of capped viral RNA by 5'–3' ligation and PCR. *Biotechniques* 10:486.

70. Maran, A.; Maitra, R. K.; Kurnar, A.; Dong, B.; Xiao, W.; Li, G.; Williams, B. R. G.; Torrence, P. F.; and Silverman, R. H. (1994). Blockage of NF-kB signaling by selective ablation of an mRNA target by antisense chimeras. *Science* 265:789–792.

71. Martell, M.; Esteban, J. I.; Quer, J.; Genesca, J.; Weiner, A.; Esteban R.; Guardia, J.; and Gomez, J. (1992). Hepatitis C virus (HCV) circulates as a population of different but closely related genomes: Quasispecies nature of the HCV genome distribution. *J. Virol.* 66:3225–3229.

72. Martell, M.; Esteban, J. I.; Quer, J., Vargas, V.; Esteban, R.; Guardia, J.; and Gomez, J. (1994). Dynamic behavior of hepatitis C virus quasispecies in patients undergoing orthotopic liver transplantation. *J. Virol.* 68:3425–3436.

73. Mast, E. E. and Alter, M. J. (1993). Epidemiology of viral hepatitis: An overview. *Semin. Virol.* 4:273–283.

74. Miyamoto, H.; Okamoto, H.; Sato, K.; Tanaka, T.; and Mishiro, S. (1992). Extraordinarily low density of hepatitis C virus estimated by sucrose density centrifugation and polymerase chain reaction. *J. Gen. Virol.* 73:715–718.

75. Mizushima, H.; Hijikata, H.; Asabe, S.-I.; Hirota, M.; Kirnura, K.; and Shimotohno, K. (1994). Two hepatitis C virus glycoprotein E2 products with different C termini. *J. Virol.* 68:6215–6222.

76. Moldvay, J.; Deny, P.; Pol, S.; Brechot, C.; and Lamas, E. (1994). Detection of hepatitis C virus RNA in peripheral blood mononuclear cells of infected patients by in situ hybridization. *Blood* 83:269–273.

77. Moore, M. J. and Sharp, P. A. (1992). Site-specific modification of pre-mRNA: The 2'-hydroxyl groups at the splice sites. *Science* 256:992–997.

78. Muller, H. M.; Pfaff, E.; Goeser, T.; Kallinowski, B.; Solbach, C.; and Theilmann, L. (1993). Peripheral blood leukocytes serve as a possible extrahepatic site for hepatitis C virus replication. *J. Gen. Virol.* 74:669–676.

79. Negro, F.; Pacchioni, D.; Shimizu, Y.; Miller, R. H.; Bussolati, G.; Purcell, R. H.; and Bonino, F. (1992). Detection of intrahepatic replication of hepatitis C virus RNA by in situ hybridization and comparison with histopathology. *Proc. Nati. Acad. Sci. USA* 89:2247–2251.

80. Nouri Aria, K. T.; Sallie, R.; Sangar, D.; Alexander, G. J.; Smith, H.; Byrne, J.; Portmann, B.; Eddleston, A. L.; and Williams, R. (1993). Detection of genomic and intermediate replicative strands of hepatitis C virus in liver tissue by in situ hybridization. *J. Clin. Inves.* 91:2226–2234.

81. Nuovo, G. J.; Lidonnici, K.; MacConnell, P.; and Lane, B. (1993). Intracellular localization of polymerase chain reaction (PCR)-amplified hepatitis C cDNA. *Amer. J. Surg. Path.* 17:683–690.

82. Ogata, N.; Alter, H. J.; Miller, R. H.; and Purcell, R. H. (1991). Nucleotide sequence and mutation rate of the H strain of hepatitis C virus. *Proc. Natl. Acad. Sci. USA* 88:3392–3396.

83. Okamoto, H.; Kojima, M.; Okada, S.-I.; Yoshizawa, H.; Iizuka, H.; Tanaka, T.; Muchmore, E. E.; Peterson, D. A.; Ito, Y.; and Mishiro, S. (1992). Genetic drift of hepatitis C virus during an 8.2 year infection in a chimpanzee: Variability and stability. *Virology* 190:894–899.

84. Okamoto, H.; Kojima, M.; Sakamoto, M.; Iizuka, H.; Hadiwandowo, S.; Suwignyo, S.; Miyakawa, Y.; and Mayurni, M. (1994). The entire nucleotide sequence and classification of a hepatitis C virus isolate of a novel genotype from an Indonesian patient with chronic liver disease. *J. Gen. Virol.* 75:629–635.

85. Okamoto, H.; Okada, S.; Sugiyama, Y.; Kurai, K.; Iizuka, H.; Machida, A.; Miyakawa, Y.; and Mayumi, M. (1991). Nucleotide sequence of the genomic RNA of hepatitis C virus isolated from a human carrier: comparison with reported isolates for conserved and divergent regions. *J. Gen. Virol.* 72:2697–2704.

86. Prince, A.; Brotman, B.; Huima, T.; Pascual, D.; Jaffery, M.; and Inchauspe, G. (1992). Immunity in hepatitis C infection. *J. Infect. Dis.* 165:438–443.

87. Ralston, R.; Thudium, K.; Berger, K.; Kuo, C.; Gervase, B.; Hall, J.; Selby, M.; Kuo, G.; Houghton, M.; and Choo, Q.-L. (1993). Characterization of hepatitis C virus envelope glycoprotein complexes expressed by recombinant vaccinia viruses. *J. Virol.* 67:6753–6761.

88. Rice, C. M.; and Walker, C. M. (1995). Hepatitis C virus (HCV)-specific T lymphocyte responses and the pathogenesis of chronic HCV infection. *Curr. Opin. Immunol.* In press.

89. Rice, C. M. (1995). Flaviviridae: The viruses and their replication. In *"Fields Virology"* (B. N. Fields, D. M. Knipe and P. M. Howley, Eds.), Third Edition, pp. 931–959, Raven Press, New York.

90. Rice, C. M.; Lenches, E. M.; Eddy, S. R.; Shin, S. J.; Sheets, R. L.; and Strauss, J. H. (1985). Nucleotide sequence of yellow fever virus: Implications for flavivirus gene expression and evolution. *Science* 229:726–733.

91. Sakamoto, M.; Akahane, Y.; Tsuda, F., Tanaka, T.; Woodfield, D. G.; and Okamoto, H. (1994). Entire nucleotide sequence and characterization of a hepatitis C virus of genotype V/3a. *J. Gen. Virol.* 75:1761–1768.

92. Sato, K.; Okamoto, H.; Aihara, S.; Hoshi, Y.; Tanaka, T.; and Mishiro, S. (1993). Demonstration of sugar moiety on the surface of hepatitis C virions recovered from the circulation of infected humans. *Virology* 196:354–357.

93. Selby, M. J.; Glazer, E.; Masiarz, F.; and Houghton, M. (1994). Complex processing and protein: Protein interactions in the E2:NS2 region of HCV. *Virology* 204:114–122.

94. Sherker, A. H.; Twu, J. S.; Reyes, G. R.; and Robinson, W. S. (1993). Presence of viral replicative intermediates in the liver and serum of patients infected with hepatitis C virus. *J. Med. Virol.* 39:91–96.

95. Shimizu, Y.; Feinstone, S. M.; Hijikata, M.; Iwamoto, A.; Purcell, R. H.; and Yoshikura, H. (1994a). Hepatitis C virus: Detection by electron microscopy of intracellular virus particles. Submitted.

96. Shimizu, Y. K.; Hijikata, M.; Iwainoto, A.; Alter, H. J.; Purcell, R. H.; and Yoshikura, H. (1994b). Neutralizing antibodies against hepatitis C virus and the emergence of neutralization escape mutant viruses. *J. Virol.* 68:1494–1500.

97. Shimizu, Y. K.; Iwamoto, A.; Hijikata, M.; Purcell, R. H.; and Yoshikura, H. (1992). Evidence for in vitro replication of hepatitis C virus genome in a human T-cell line. *Proc. Natl. Acad. Sci USA* 89:5477–5481.

98. Shimizu, Y. K.; Purcell, R. H.; and Yoshikura, H. (1993). Correlation between the infectivity of hepatitis C virus in vivo and its infectivity in vitro. *Proc. Natl. Acad. Sci. USA* 90:6037–6041.

99. Shimizu, Y. K.; Weiner, A. J.; Rosenblatt, J.; Wong, D. C.; Shapiro, M.; Popkin, T.; Houghton, M.; Alter, H. J.; and Purcell, R. H. (1990). Early events in hepatitis C virus infection of chimpanzees. *Proc. Natl. Acad. Sci. USA* 87:6441–6444.

100. Simmonds, P.; Smith, D. B.; McOmish, F.; Yap, P. L.; Kolberg, J.; Urdea, M. S.; and Holmes, E. C. (1994). Identification of genotypes of hepatitis C virus by sequence comparisons in the core, E1 and NS5 regions. *J. Gen. Virol.* 75:1053–1061.

101. Simons, J. N.; Pilot-Matias, T. J.; Leary, T. P.; Dawson, G. J.; Desai, S. M.; Schlauder, G. G.; Muerhoff, A. S.; Erker, J. C.; Buijk, S. L.; Chalmers, M. L.; and et al. (1995). Identification of two flavivirus-like genomes in the GB hepatitis agent. *Proc. Natl. Acad. Sci. USA* 92:3401–3405.

102. Spaete, R. R.; Alexander, D.; Rugroden, M. E.; Choo, Q.-L.; Berger, K.; Crawford, K.; Kuo, C.; Leng, S.; Lee, C.; Ralston, R.; Thudium, K.; Tung, J. W.; Kuo, G.; and Houghton, M. (1992). Characterization of the hepatitis E2/NS1 gene product expressed in mammalian cells. *Virology* 188:819–830.

103. Sullenger, B. A.; Gallardo, H. F.; Ungers, G. E.; and Gilboa, E. (1990). Overexpression of TAR sequences renders cells resistant to human immunodeficiency virus replication. *Cell* 63:601–608.

104. Suzich, J. A.; Tamura, J. K.; Palmer-Hill, F.; Warrener, P.; Grakoui, A.; Rice, C. M.; Feinstone, S. M.; and Collett, M. S. (1993). Hepatitis C virus NS3 protein polynucleotide-stimulated nucleoside triphosphatase and comparison with the related pestivirus and flavivirus enzymes. *J. Virol.* 67:6152–6158.

105. Tabor, E.; Garety, R. J.; Drucker, J. A.; Seeff, L. B.; Hoofnagle, J. F.; Jackson, D. R.; April, M.; Barker, L. F.; and Pineda-Tamondong, G. (1978). Transmission of non-A, non-B hepatitis from man to chimpanzee. *Lancet* 1:463–466.

106. Takahashi, K.; Kishimoto, S.; Yoshizawa, H.; Okamoto, H.; Yoshikawa, A.; and Mishiro, S. (1992). p26 protein and 33-nm particle associated with nucleocapsid of hepatitis C virus recovered from the circulation of infected hosts. *Virology* 191: 431–434.

107. Takehara, T.; Hayashi, N.; Mita, E.; Hagiwara, H.; Ueda, K.; Katayama, K.; Kasahara, A.; Fusamoto, H.; and Kamada, T. (1992). Detection of the minus strand of hepatitis C virus RNA by reverse transcription and polymerase chain reaction: Implications for hepatitis C virus replication in infected tissue. *Hepatology* 15:387–390.

108. Tanaka, Y.; Enomoto, N.; Kojima, S.; Tang, L.; Goto, M.; Marumo, F.; and Sato, C. (1993). Detection of hepatitis C virus RNA in the liver by in situ hybridization. *Liver* 13:203–208.

109. Taniguchi, S.; Okamoto, H.; Sakamoto, M.; Kojima, M.; Tsuda, F.; Tanaka, T.; Munekata, E.; Muchmore, E. E.; Peterson, D. A.; and Mishiro, S. (1993). A structurally flexible and antigenically variable N-terminal domain of the hepatitis C virus E2/NS1 protein: Implication for an escape from antibody. *Virology* 195:297–301.

110. Thomssen, R.; Bonk, S.; Propfe, C.; Heermann, K. H.; Kochel, H. G.; and Uy, A. (1992). Association of hepatitis C virus in human sera with beta-lipoprotein. *Med. Microbiol. Immunol.* 181 293–300.

111. Thomssen, R.; Bonk, S.; and Thiele, A. (1993). Density heterogeneities of hepatitis C virus in human sera due to the binding of beta-lipoproteins and immunoglobulins. *Med. Microbiol. Immunol.* 182:329–334.

112. Tokita, H.; Shrestha, S. M.; Okamoto, H.; Sakamoto, M.; Horikita, M.; Iizuka, H.; Shrestha, S.; Miyakawa, Y.; and Mayumi, M. (1994). Hepatitis C virus variants from Nepal with novel genotypes and their classification into the third major group. *J. Gen. Virol.* 75:931–936.

113. Tsukiyama-Kohara, K.; Iizuka, N.; Kohara, M.; and Nomoto, A. (1992). Internal ribosome entry site within hepatitis C virus RNA. *J. Virol.* 66:1476–1483.

114. Wang, C.; Sarnow, P.; and Siddiqui, A. (1993). Translation of human hepatitis C virus RNA in cultured cells is mediated by an internal ribosome-binding mechanism. *J. Virol.* 67:3338–3344.

115. Wang, J. T.; Sheu, J. C.; Lin, J. T.; Wang, T. H.; and Cheni, D. S. (1992). Detection of replicative form of hepatitis C virus RNA in peripheral blood mononuclear cells. *J. Inf. Dis.* 166:1167–1169.

116. Weiner, A. J.; Brauer, M. J.; Rosenblatt, J.; Richman, K. H.; Tung, J.; Crawford, K.; Bonino, F.; Saracco, G.; Clhoo, Q.-L.; Houghton, M.; and Han, J. H. (1991). Variable and hypervariable domains are found in the regions of HCV corresponding to the flavivirus envelope and NSI proteins and the pestivirus envelope glycoproteins. *Virology* 180:842–848.

117. Weiner, A. J.; Geysen, H. M.; Christopherson, C.; Hall, J. E.; Mason, T. J.; Saracco, G.; Bonino, F.; Crawford, K.; Marion, C. D.; Crawford, K. A.; Brunetto, M.; Barr, P. J.; Miyamura, T.; McHutchinson, J.; and Houghton, M. (1992). Evidence for immune selection of hepatitis C virus (HCV) putative envelope glycoprotein variants: Potential role in chronic HCV infections. *Proc. Nati. Acad. Sci. USA* 89:3468–3472.

118. Wright, T. L.; Combs, C.; Kim, M.; Ferrell, L.; Bacchetti, P.; Ascher, N.; Roberts, J.; Wilber, J.; Sheridan, P.; and Urdea, M. (1994). Interferon-alpha therapy for hepatitis C virus infection after liver transplantation. *Hepatology* 20:773–779.

119. Yamada, G.; Nishimoto, H.; Endou, H.; Doi, T.; Takahashi, M.; Tsuji, T.; Yoshizawa, H.; Nozawa, M.; Koji, T.; and Nakane, P. K. (1993). Localization of hepatitis C viral RNA and capsid protein in human liver. *Digest. Dis. Sci.* 38:882–887.

120. Yoo, B. J.; Selby, M.; Choe, J.; Suh, B. S.; Choi, S. H.; Joh, J. S.; Nuovo, G. J.; Lee, H.-S.; Houghton, M.; and Han, J. H. (1995). Transfection of a differentiated human hepatoma cell line (Huh7) with in vitro-transcribed hepatitis C virus (HCV) RNA and establishment of a long-term culture persistently infected with HCV. *J. Virol.* 69:32–38.

121. Yoo, B. J.; Spaete, R. R.; Geballe, A. P.; Selby, M.; Houghton, M.; and Han, J. H. (1992). 5' end-dependent translation initiation of hepatitis C viral RNA and the presence of putative positive and negative translational control elements within the 5' untranslated region. *Virology* 191:889–899.

122. Young, K. C.; Chang, T. T.; Liou, T. C.; and Wu, H. L. (1993). Detection of hepatitis C virus RNA in peripheral blood mononuclear cells and in saliva. *J. Med. Virol.* 41:55–60.

123. Yuasa, T.; Ishikawa, G.; Manabe, S.; Sekiguchi, S.; Takeuchi, K.; and Miyamura, T. (1991). The particle size of hepatitis C virus estimated by filtration through microporous regenerated cellulose fibre. *J. Gen. Virol.* 72:2021–2024.

124. Yun, Z. B.; Lindh, G.; Weiland, O.; Johansson, B.; and Sonnerborg, A. (1993). Detection of hepatitis C virus (HCV) RNA by PCR related to HCV antibodies in serum and liver histology in Swedish blood donors. *J. Med. Virol.* 39:57–61.

125. Zeiner, M. and Gehring, U. (1994). Cloning of 5' cDNA regions by inverse PCR. *BioTechniques* 17:1051–1053.

126. Zibert, A.; Schreier, E.; and Roggendorf, M. (1995). Antibodies in human sera specific to hypervariable region 1 of hepatitis C virus can block viral attachment. *Virology* 208:653–661.

127. Zignego, A. L.; Macchia, D.; Monti, M.; Thiers, V.; Mazzetti, M.; Foschi, M.; Maggi, E.; Romagnanii, S.; Gentilini, P.; and Brechot, C. (1992). Infection of peripheral mononuclear blood cells by hepatitis C virus. *J. Hepatol.* 15:382–386.

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

```
AAUGGUGGCU CCAUCUUAGC CCUAGUCACG GCUAGCUGUG AAAGGUCCGU GAGCCGCAUG        60
ACUGCAGAGA GUGCUGAUAC UGGCCUCUCU GCWGAUCAUG U                           101
```

( 2 ) INFORMATION FOR SEQ ID NO:2:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:2:

```
ACAUGAUCWG CAGAGAGGCC AGUAUCAGCA CUCUCUGCAG UCAUGCGGCU CACGGACCUU        60
UCACAGCUAG CCGUGACUAG GGCUAAGAUG GAGCCACCAU U                           101
```

( 2 ) INFORMATION FOR SEQ ID NO:3:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AATGGTGGCT CCATCTTAGC CCTAGTCACG GCTAGCTGTG AAAGGTCCGT GAGCCGCATG        60
ACTGCAGAGA GTGCTGATAC TGGCCTCTCT GCWGATCATG T                           101
```

( 2 ) INFORMATION FOR SEQ ID NO:4:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ACATGATCWG CAGAGAGGCC AGTATCAGCA CTCTCTGCAG TCATGCGGCT CACGGACCTT        60
TCACAGCTAG CCGTGACTAG GGCTAAGATG GAGCCACCAT T                           101
```

( 2 ) INFORMATION FOR SEQ ID NO:5:

( i ) SEQUENCE CHARACTERISTICS:
        ( A ) LENGTH: 27 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GACTGTTGTG GCCTGCAGGG CCGAATT 27

( 2 ) INFORMATION FOR SEQ ID NO:6:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

TTGAATTCGA CCCTGCAGGC CACAACA 27

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

TTGAATTCGG CCCTGCAGGC CACAACAGTC 30

( 2 ) INFORMATION FOR SEQ ID NO:8:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CAAGTCGACG GGGAGACATT TATCACAGC 29

( 2 ) INFORMATION FOR SEQ ID NO:9:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

TGAAGATTGG GCTAACCACT CC 22

( 2 ) INFORMATION FOR SEQ ID NO:10:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
  ( A ) NAME/KEY: misc_feature
  ( B ) LOCATION: 27
  ( D ) OTHER INFORMATION: /product= "NUCLEOTIDE REPEAT"

( x i ) SEQUENCE DESCRIPTION: SEQ ID NO:10:

TGAAGGTTGG GTAAACACTC CGGCCTA    27

( 2 ) INFORMATION FOR SEQ ID NO:11:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 45
  ( D ) OTHER INFORMATION: /product= "NUCLEOTIDE REPEAT"

( x i ) SEQUENCE DESCRIPTION: SEQ ID NO:11:

TGAAGGTTGG GGTAAACACT CCGGCCTCTT AGGCCATTTC CTGTT    45

( 2 ) INFORMATION FOR SEQ ID NO:12:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 46
  ( D ) OTHER INFORMATION: /product= "NUCLEOTIDE REPEAT"

( x i ) SEQUENCE DESCRIPTION: SEQ ID NO:12:

TAAAGGTTGG GGTAAACACT CCGGCCTCTT AGGCCATTTT CTGTGT    46

( 2 ) INFORMATION FOR SEQ ID NO:13:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 41
  ( D ) OTHER INFORMATION: /product= "NUCLEOTIDE REPEAT"

( x i ) SEQUENCE DESCRIPTION: SEQ ID NO:13:

TGAACGGGGA GATAAACACT CCAGGCCAAT AGGCCATCCC T    41

( 2 ) INFORMATION FOR SEQ ID NO:14:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 42
  ( D ) OTHER INFORMATION: /product= "NUCLEOTIDE REPEAT"

( x i ) SEQUENCE DESCRIPTION: SEQ ID NO:14:

TGAACGGGGA GCTAAACACT CCAGGCCAAT AGGCCATCCT GT 42

( 2 ) INFORMATION FOR SEQ ID NO:15:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 46
    ( D ) OTHER INFORMATION: /product= "NUCLEOTIDE REPEAT"

( x i ) SEQUENCE DESCRIPTION: SEQ ID NO:15:

TGAACGGGGA GCTAAACACT CCAGCCAATA GGCCATTTCC TTTTGT 46

( 2 ) INFORMATION FOR SEQ ID NO:16:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 42
    ( D ) OTHER INFORMATION: /product= "NUCLEOTIDE REPEAT"

( x i ) SEQUENCE DESCRIPTION: SEQ ID NO:16:

TAGAGCGGCA CACTTAGCTA CACTCCATAG CTAACTGTCC CT 42

( 2 ) INFORMATION FOR SEQ ID NO:17:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 42
    ( D ) OTHER INFORMATION: /product= "NUCLEOTIDE REPEAT"

( x i ) SEQUENCE DESCRIPTION: SEQ ID NO:17:

TAGAGCGGCA AACCCTAGCT ACACTCCATA GCTAGTTTCC GT 42

( 2 ) INFORMATION FOR SEQ ID NO:18:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
  ( A ) NAME/KEY: misc_feature
  ( B ) LOCATION: 35
  ( D ) OTHER INFORMATION: /product= "NUCLEOTIDE REPEAT"

( x i ) SEQUENCE DESCRIPTION: SEQ ID NO:18:

TGAGCTGGTA AGATAACACT CCATTTCTTT TTTGT  35

( 2 ) INFORMATION FOR SEQ ID NO:19:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 32
    ( D ) OTHER INFORMATION: /product= "NUCLEOTIDE REPEAT"

( x i ) SEQUENCE DESCRIPTION: SEQ ID NO:19:

TGAGCTGGTA GGTTAACACC CCAACCCTGT GT  32

( 2 ) INFORMATION FOR SEQ ID NO:20:

( i ) SEQUENCE CHARACTERISTICS:
    ( A ) LENGTH: 285 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

GTGTCTCATG CCCGGCCCCG CTGGTTCTGG TTTTGCCTAC TCCTGCTCAC TGCAGGGGTA  60
GGTATCTACC TCCTCCCCAA CCGATGAAGG TTGGGGTAAA CACTCCGGCC TCTTAGGCCA  120
TTTCCTGTTT TTTTTTTTTT TTTTTTTCTT TCCTTCTTTT TTCCTTTCTT TTCCTTCCTT  180
CTTTAATGGT GGCTCCATCT TAGCCCTAGT CACGGCTAGC TGTGAAAGGT CCGTGAGCCG  240
CATGACTGCA GAGAGTGCTG ATACTGGCCT CTCTGCAGAT CATGT  285

( 2 ) INFORMATION FOR SEQ ID NO:21:

( i ) SEQUENCE CHARACTERISTICS:
    ( A ) LENGTH: 298 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

GTGTCTCATG CCCGGCCCCG CTGGTTCTGG TTTTGCCTAC TCCTGCTCGC TGCAGGGGTA  60
GGCATCTACC TCCTCCCCAA CCGATGAAGG TTGGGGTAAA CACTCCGGCC TCTTAGGCCA  120
TTTCCTGTTT TTTTTTTTTT TTTTTTTTTT TTTTTTTTTC TTTTCCTTCT TTTTCCCTTT  180
TTCTTTCTTC CTTCTTTAAT GGTGGCTCCA TCTTAGCCCT AGTCACGGCT AGCTGTGAAA  240
GGTCCGTGAG CCGCATGACT GCAGAGAGTG CTGATACTGG CCTCTCTGCA GATCATGT  298

( 2 ) INFORMATION FOR SEQ ID NO:22:

( i ) SEQUENCE CHARACTERISTICS:

(A) LENGTH: 356 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

| | | | | | | |
|---|---|---|---|---|---|---|
| GTGTCTCATG | CCCGGCCCCG | CTGGTTCTGG | TTTTGCCTAC | TCCTGCTCGC | TGCAGGGGTA | 60 |
| GGCATCTACC | TCCTCCCCAA | CCGATGAAGG | TTGGGGTAAA | CACTCCGGCC | TCTTAGGCCA | 120 |
| TTTCCTGTTT | TTTTTTTTT | TTTTTTTTT | TTTTTTTTT | TTTTTTTTT | TTTTTTTCT | 180 |
| TTTTTTTTT | TTTTTCCTT | TTTTTTTTT | TTTTTTTCT | TTCCTTCTTT | TTTCCTTTCT | 240 |
| TTTCCTTCCT | TCTTAATGG | TGGCTCCATC | TTAGCCCTAG | TCACGGCTAG | CTGTGAAAGG | 300 |
| TCCGTGAGCG | GCATGACTGC | AGAGAGTGCT | GATACTGGCC | TCTCCGCAGA | TCATGT | 356 |

(2) INFORMATION FOR SEQ ID NO:23:

(i) SEQUENCE CHARACTERISTICS:
(A) LENGTH: 321 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

| | | | | | | |
|---|---|---|---|---|---|---|
| GTGTCTCATG | CCCGGCCCCG | CTGGTTCTGG | TTTTGCCTAC | TCCTGCTCGC | TGCAGGGGTA | 60 |
| GGCATCTACC | TCCTCCCCAA | CCGATGAAGG | TTGGGGTAAA | CACTCCGGCC | TCTTAGGCCA | 120 |
| TTTCCTGTTT | TTTTTTTTT | TCCCTTTTTT | TTTTTTTTT | TTTTTTTTT | TTTTTTTTT | 180 |
| TCTTTCCTTC | TTTTTTTCC | TTTCTTTCC | TTCCTTCTTT | AATGGTGGCT | CCATCTTAGC | 240 |
| CCTAGTCACG | GCTAGCTGTG | AAAGGTCCGT | GAGCGGCATG | ACTGCAGAGA | GTGCTGATAC | 300 |
| TGGCCTCTCT | GCTGATCATG | T | | | | 321 |

(2) INFORMATION FOR SEQ ID NO:24:

(i) SEQUENCE CHARACTERISTICS:
(A) LENGTH: 257 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

| | | | | | | |
|---|---|---|---|---|---|---|
| GTGTCTCATG | CCCGGCCCCG | CTGGTTCTGG | TTTTGCCTAC | TCCTGCTTGC | TGCAGGGGTA | 60 |
| GGCATCTACC | TCCTCCCCAA | CCGATGAAGG | TTGGGGTAAA | CACTCCGGCC | TCTTAGGCCA | 120 |
| TTTCCTGTTT | TTTTTTTTT | TTTTTTTTT | TTTTTTTTT | TTTTTTTTT | TTTTTTTTT | 180 |
| TCTTTCCTTC | CTTTTTCCCT | TTCTTTTCTT | CCTTCTTTAA | TGGTGGCTCC | ATCTTAGCCC | 240 |
| TAGTCACGGC | TAGCTGT | | | | | 257 |

(2) INFORMATION FOR SEQ ID NO:25:

(i) SEQUENCE CHARACTERISTICS:
(A) LENGTH: 253 base pairs
(B) TYPE: nucleic acid
(C) STRANDEDNESS: single
(D) TOPOLOGY: linear (ii) MOLECULE TYPE: RNA (genomic)

( x i ) SEQUENCE DESCRIPTION: SEQ ID NO:25:

| | | | | | | |
|---|---|---|---|---|---|---|
| CUCCCCAACC | GAUGAAGGUU | GGGGUAAACA | CUCCGGCCUC | UUAGGCCAUU | UCCUGUUUUU | 60 |
| UUUUUUUUUU | UUUUUUUUUU | UUUUUUUUUU | UUUUUUUUUU | UUUUUUUUUU | UUUCUUUCCU | 120 |
| UCUUUUUUUU | CCUUUCUUUU | CCUUCCUUCU | UUAAUGGUGG | CUCCAUCUUA | GCCCUAGUCA | 180 |
| CGGCUAGCUG | UGAAAGGUCC | GUGAGCGGCA | UGACUGCAGA | GAGUGCUGAU | ACUGGCCUCU | 240 |
| CUGCAGAUCA | UGU | | | | | 253 |

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

| | | | |
|---|---|---|---|
| TAACATGATC | AGCAGAGAGG | CCAG | 24 |

( 2 ) INFORMATION FOR SEQ ID NO:27:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

| | | |
|---|---|---|
| CTCACGGACC | TTTCACAGC | 19 |

( 2 ) INFORMATION FOR SEQ ID NO:28:

( i ) SEQUENCE CHARACTERISTICS:
        ( A ) LENGTH: 227 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

| | | | | | | |
|---|---|---|---|---|---|---|
| CTGTCTCGTG | CCCGACCCCG | CTGGTTCATG | TTGTGCCTAC | TCCTACTTTC | CGTAGGGGTA | 60 |
| GGCATCTACC | TGCTCCCCAA | CCGATGAACG | GGGAGCTAAC | ACTCCAGGCC | AATAGGCATC | 120 |
| CTGTTTTTTT | TTTTTTTTTT | TTTTTTTTTT | TTTTTTTTTT | TTTTTTTTTT | TTTTTTTTTT | 180 |
| TTTTTTTCTT | TTCTTTGGTG | GCTCCATCTT | AGCCCTAGTC | ACGGCTA | | 227 |

( 2 ) INFORMATION FOR SEQ ID NO:29:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

| | | | | | | |
|---|---|---|---|---|---|---|
| GTGTCACGTG | CCCGAACCCG | CTATTTGCTG | CTTTGCCTAC | TCCTACTAAC | GGTAGGGGTA | 60 |
| GGCATCTTTC | TCCTGCCAGC | GCGATGAGCT | GGTAGGATAA | CACTCCATTT | CTTTTTTTGT | 120 |

| | | | | | | |
|---|---|---|---|---|---|---|
| TTTTTTTTT | TTTTTTTTT | TTTTTTTTT | TTTTTTTTT | TTTTTTTTT | TTTTTTTTT | 180 |
| TTTTTCTTT | TTCTTTCCTT | TCTTTCTGA | CTTCTAATTT | TCCTTCTTAG | GTGGCTCCAT | 240 |
| CTTAGCCCTA | GTCACGGCTA | | | | | 260 |

(2) INFORMATION FOR SEQ ID NO:30:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

| | | | | | | |
|---|---|---|---|---|---|---|
| GTGTCCCATG | CCCGACCCCG | CTATCTACTC | CTGTGCCTAC | TCCTACTTTC | CGTAGGGTA | 60 |
| GGCATCTTCC | TGCTGCCTGC | TCGATAGGCA | GCTTAACACT | CCGACCTTAG | GGTCCTTCTG | 120 |
| TTTTTTTTT | TTTTTTTTT | TTTTTTTTT | TTTTTTTTT | TTTTTTTTT | TTTTTTTTT | 180 |
| TTTTTTTTT | TTTTTTTCC | TTACCCTTTC | CTTCTTTTCT | TCCTTTTTTT | TCCTTACTTG | 240 |
| GTGGCTCCAT | CTTAGCCCTA | GTCACGGCTA | | | | 270 |

(2) INFORMATION FOR SEQ ID NO:31:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

| | | | | | | |
|---|---|---|---|---|---|---|
| ATGTCTCATG | CCCGACCCCG | CTATTTACTC | CTGTGCCTAC | TCCTACTTAC | AGTAGGGTA | 60 |
| GGCATCTTCC | TGCTGCCTGC | TCGGTAGGCA | GCTTAACACT | CCGACCTTAG | GGTCCCCTTG | 120 |
| TTTTTTTTT | TTCTTTCCTT | CTTTCCTTTC | CTAATCTTTC | TTTCTTGGTG | GCTCCATCTT | 180 |
| AGCCCTAGTC | ACGGCTA | | | | | 197 |

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

| | | |
|---|---|---|
| CCAAGAATTC CCTAGTCACG GCTAGC | | 26 |

(2) INFORMATION FOR SEQ ID NO:33:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

| | | | | | | |
|---|---|---|---|---|---|---|
| GCTGTGAAAG | GTCCGTGAGC | CGCATGACTG | CAGAGAGTGC | TGAAACTGGC | CTCTCTGCAG | 60 |

ATCATGT 67

(2) INFORMATION FOR SEQ ID NO:34:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:34:

GCTGTGAAAG GTCCGTGAGC CGCTTGACTG CAGAGAGTGC TGATACTGGC CTCTCTGCAG 60

ATCAAGT 67

(2) INFORMATION FOR SEQ ID NO:35:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:35:

GCTGTGAAAG GTCCGTGAGC CGCATGACTG CAGAGAGTGC TGATACTGGC CTCTCTGCAG 60

ATCATGT 67

(2) INFORMATION FOR SEQ ID NO:36:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:36:

GCTGTGAAAG GTCCGTGAGC CGCATGACTG CAGAGAGTGC TGAAACTGGC CTCTCTGCAG 60

ATCATGT 67

(2) INFORMATION FOR SEQ ID NO:37:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:37:

CGCACCCTGT CCGACTACAA CATCC 25

(2) INFORMATION FOR SEQ ID NO:38:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:38:

```
CAGAATTCTT GTAGTCGGAC AGGGTGCG                                                  2 8
```

( 2 ) INFORMATION FOR SEQ ID NO:39:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

```
GCCAGCCCCC TGATGGGGGC GACACTCCAC CATGAAATC                                      3 9
```

What is claimed is:

1. An isolated polynucleotide comprising a nucleic acid molecule which specifically hybridizes to a nucleic acid molecule of SEQ ID NO:1, SEQ ID NO:2, SEQ ID NO:3, SEQ ID NO:4, SEQ ID NO:33, SEQ ID NO:34, SEQ ID NO:35 or SEQ ID NO:36.

2. The isolated polynucleotide of claim 1 wherein the nucleic acid molecule is an HCV 3' terminal sequence element.

3. The isolated polynucleotide of claim 2 comprising SEQ ID NO:1, SEQ ID NO:2, SEQ ID NO:3, SEQ ID NO:4, SEQ ID NO:33, SEQ ID NO:34, SEQ ID NO:35 or SEQ ID NO:36.

4. The polynucleotide of claim 1 which is operably linked to an expression control sequence.

5. A host cell transformed or transfected with the polynucleotide of claim 4.

6. The host cell of claim 5, wherein the host cell is a mammalian cell.

7. The host cell of claim 6, wherein the host cell is a human cell.

8. The host cell of claim 7, wherein the host cell is a hepatocyte.

9. The isolated polynucleotide of claim 7 comprising a recombinant DNA or RNA molecule having an HCV sequence which includes the 3' terminal sequence element.

10. The isolated polynucleotide of claim 9 wherein the HCV is HCV-1, HC-J1, HC-J, HCV-BK, HCV-H, HC-J6, HC-J8, HC-J483, HC-J491, HC-C2, HCV-JK, HCV-N HCV-T, HCV-JT, HC-G9, HCV-K3a, NZL1, or HCV-Tr.

11. The isolated polynucleotide according to claim 2 wherein said nucleic acid molecule comprises a replication competent nucleic acid which includes a 3' terminal sequence element.

12. The isolated polynucleotide according to claim 11 wherein the replication competent nucleic acid is a replication competent HCV RNA.

13. A cell line transformed or transfected with the polynucleotide of claim 9.

14. A cell line transformed or transfected with the polynucleotide of claim 10.

15. A cell line transformed or transfected with the polynucleotide of claim 11.

16. An oligonucleotide comprising at least 15 nucleotides wherein said oligonucleotide specifically hybridizes to a Hepatitis C virus 3' terminal sequence element of SEQ ID NO:1, SEQ ID NO:2, SEQ ID NO:3, SEQ ID NO:4, SEQ ID NO:33, SEQ ID NO:34, SEQ ID NO:35 or SEQ ID NO:36.

17. An oligonucleotide primer suitable for initiating synthesis of a primer extension product encompassing a segment of a 3' terminal sequence element wherein said primer specifically hybridizes to a Hepatitis C virus 3' terminal sequence element of SEQ ID NO:1, SEQ ID NO:2, SEQ ID NO:3, SEQ ID NO:4, SEQ ID NO:33, SEQ ID NO:34, SEQ ID NO:35 or SEQ ID NO:36.

\* \* \* \* \*

UNITED STATES PATENT AND TRADEMARK OFFICE
CERTIFICATE OF CORRECTION

| | | |
|---|---|---|
| PATENT NO. | : 5,874,565 | Page 1 of 4 |
| APPLICATION NO. | : 08/520678 | |
| DATED | : February 23, 1999 | |
| INVENTOR(S) | : Charles M. Rice et al. | |

It is certified that error appears in the above-identified patent and that said Letters Patent is hereby corrected as shown below:

In the Sequence Listing (Column 41-44), the listing for SEQ ID NO:10 should be amended as shown to reflect an insertion of one (1) G residue at position 10:

```
(2) INFORMATION FOR SEQ ID NO:10:

(i) SEQUENCE CHARACTERISTICS:
        (A) LENGTH: 27-base 28 bases pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: [[27]] 28
        (D) OTHER INFORMATION: /product= "NUCLEOTIDE REPEAT"

(xi) SEQUENCE DESCRIPTION: SEQ ID NO:10:
TGAAGGTTGG GGTAAACACT CCGGCCTA                                    [[27]] 28

(2) INFORMATION FOR SEQ ID NO:13:

(i) SEQUENCE CHARACTERISTICS:
        (A) LENGTH: 41-base 42 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: [[41]] 42
        (D) OTHER INFORMATION: /product= "NUCLEOTIDE REPEAT"

(xi) SEQUENCE DESCRIPTION: SEQ ID NO:13:
TGAACGGGGA GATAAACACT CCAGGCCAAT AGGCCATCCC CT                     [[41]] 42
```

UNITED STATES PATENT AND TRADEMARK OFFICE
CERTIFICATE OF CORRECTION

PATENT NO. : 5,874,565  
APPLICATION NO. : 08/520678  
DATED : February 23, 1999  
INVENTOR(S) : Charles M. Rice et al.

Page 2 of 4

It is certified that error appears in the above-identified patent and that said Letters Patent is hereby corrected as shown below:

(2) INFORMATION FOR SEQ ID NO:21:

(i) SEQUENCE CHARACTERISTICS:
        (A) LENGTH: ~~298 base~~ 300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

| | | | | | |
|---|---|---|---|---|---|
| GTGTCTCATG | CCCGGCCCCG | CTGGTTCTGG | TTTTGCCTAC | TCCTGCTCGC | TGCAGGGGTA | 60 |
| GGCATCTACC | TCCTCCCCAA | CCGATGAAGG | TTGGGGTAAA | CACTCCGGCC | TCTTAGGCCA | 120 |
| TTTCCTGTT | TTTTTTTTT | TTTTTTTTT | TTTTTTTTT_TCTTTTCCTT | CTTTTTCCCT | 180 |
| TTTTCTTTCT | TCCTTCTTTA | ATGGTGGCTC | CATCTTAGCC | CTAGTCACGG | CTAGCTGTGA | 240 |
| AAGGTCCGTG | AGCCGCATGA | CTGCAGAGAG | TGCTGATACT | GGCCTCTCTG | CAGATCATGT | [[298]] 300 |

(2) INFORMATION FOR SEQ ID NO:24:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

| | | | | | |
|---|---|---|---|---|---|
| GTGTCTCATG | CCCGGCCCCG | CTGGTTCTGG | TTTTGCCTAC | TCCTGCTTGC | TGCAGGGGTA | 60 |
| GGCATCTACC | TCCTCCCCAA | CCGATGAAGG | TTGGGGTAAA | CACTCCGGCC | TCTTAGGCCA | 120 |
| TTTCCTGTT | TTTTTTTTT | TTTTTTTTT | TTTTTTTTT | TTTTTTTTT | TTTTTTTTT | 180 |
| TCTTTCCTTC | CTTTT[[T]]CCCTT | TTCTTTTCTT | CCTTCTTTAA | TGGTGGCTCC | ATCTTAGCCC | 240 |
| TAGTCACGGC | TAGCTGT | | | | | 257 |

UNITED STATES PATENT AND TRADEMARK OFFICE
CERTIFICATE OF CORRECTION

PATENT NO. : 5,874,565  
APPLICATION NO. : 08/520678  
DATED : February 23, 1999  
INVENTOR(S) : Charles M. Rice et al.

Page 3 of 4

It is certified that error appears in the above-identified patent and that said Letters Patent is hereby corrected as shown below:

```
(2) INFORMATION FOR SEQ ID NO:25:

(i) SEQUENCE CHARACTERISTICS:
        (A) LENGTH: [[253 base]] 249 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:25:
CUCCCCAACC GAUGAAGGUU GGGGUAAACA CUCCGGCCUC UUAGGCCAUU UCCUGUUUUU      60

UUUUUUUUUU UUUUUUUUUU UUUUUUUUUU UUUUUUUUUU UUUUUUUU[[U UUU]]C UUUCCUUCUU  120

UUUUUUCCUU UCUUUUCCUU CCUUCUUUAA UGGUGGCUCC AUCUUAGCCC UAGUCACGGC     180

UAGCUGUGAA AGGUCCGUGA GCGGCAUGAC UGCAGAGAGU GCUGAUACUG GCCUCUCUGC     240

AGAUCAUGU                                                      [[253]] 249
```

UNITED STATES PATENT AND TRADEMARK OFFICE
CERTIFICATE OF CORRECTION

PATENT NO. : 5,874,565
APPLICATION NO. : 08/520678
DATED : February 23, 1999
INVENTOR(S) : Charles M. Rice et al.

It is certified that error appears in the above-identified patent and that said Letters Patent is hereby corrected as shown below:

```
(2) INFORMATION FOR SEQ ID NO:30:

(i) SEQUENCE CHARACTERISTICS:
        (A) LENGTH: 270 base 271 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TTGTCCCATG CCCGACCCCG CTATCTACTC CTGTGCCTAC TCCTACTTTC CGTAGGGGTA      60
GGCATCTTCC TGCTGCCTGC TCGATAGGCA GCTTAACACT CCGACCTTAG GGTCCTTCTG     120
TTTTTTTTT  TTTTTTTTTT TTTTTTTTTT TTTTTTTTT  TTTTTTTTTT TTTTTTTTT     180
TTTTTTTTT  TTTTTTTTCC TTACCCTTTC CTTCTTTTCT TCCTTTTTTT TCCTTACTTT     240
GGTGGCTCCA TCTTAGCCCT AGTCACGGCTA                                 [[270]] 271
```

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,874,565 | |
| APPLICATION NO. | : 08/520678 | |
| DATED | : February 23, 1999 | |
| INVENTOR(S) | : Charles M. Rice et al. | |

It is certified that error appears in the above-identified patent and that said Letters Patent is hereby corrected as shown below:

Drawings:

Delete Fig. 8 and substitute therefor Fig. 8 as shown on the attached page.

Signed and Sealed this

Tenth Day of June, 2008

JON W. DUDAS
*Director of the United States Patent and Trademark Office*

```
1b   GCTGTGAAAG GTCCGTGAGC CGCATGACTG CAGAGAGTGC TGAAACTGGC GTCTGT
3    GCTGTGAAAG GTCCGTGAGC CGCTTGACTG CAGAGAGTGC TGATACTGGC CTCTCT
4?   GCTGTGAAAG GTCCGTGAGC CGCATGACTG CAGAGAGTGC TGATACTGGC CTCTCT
4a   GCTGTGAAAG GTCCGTGAGC CGCATGACTG CAGAGAGTGC TGAAACTGGC CTCTCT

1b   CTCTCTGCA GATCATGT
3    CTCTCTGCA GATCAAGT
4?   CTCTCTGCA GATCATGT
4a   CTCTCTGCA GATCATGT
```

Figure 8